United States Patent
Bini et al.

(10) Patent No.: US 12,148,014 B1
(45) Date of Patent: Nov. 19, 2024

(54) COMPUTERIZED AGGREGATION AND DISTRIBUTION ARCHITECTURE FOR DIGITAL HEALTH INFRASTRUCTURE

(71) Applicant: Express Scripts Strategic Development, Inc., St. Louis, MO (US)

(72) Inventors: Mark G. Bini, O'Fallon, MO (US); Zachary A. Goodman, St. Louis, MO (US); Sara A. Raj, St. Louis, MO (US); William S. Patterson, St. Louis, MO (US); Damian Ng, Creve Coeur, MO (US); Daniel C. Casper, Ellisville, MO (US); Ashley M. Jenne, St. Louis, MO (US); Sarah E. Ham, St. Louis, MO (US); Jamie Williams, Edwardsville, IL (US); Christina M. Vallery, Austin, TX (US); Sarah Micheletti, St. Louis, MO (US); Glen D. Stettin, Clayton, MO (US); Snezana Mahon, St. Louis, MO (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 744 days.

(21) Appl. No.: 16/875,681

(22) Filed: May 15, 2020

Related U.S. Application Data

(60) Provisional application No. 62/848,543, filed on May 15, 2019.

(51) Int. Cl.
*G06Q 30/0601* (2023.01)
*G06Q 20/12* (2012.01)
(Continued)

(52) U.S. Cl.
CPC ....... *G06Q 30/0607* (2013.01); *G06Q 20/123* (2013.01); *G06Q 30/014* (2013.01);
(Continued)

(58) Field of Classification Search
CPC ............ G06Q 30/0607; G06Q 20/123; G06Q 30/014; G06Q 30/0185; G06Q 30/0203;
(Continued)

(56) References Cited

U.S. PATENT DOCUMENTS

| | | | |
|---|---|---|---|
| 7,509,288 | B2 | 3/2009 | Bennett |
| 8,639,629 | B1 | 1/2014 | Hoffman |

(Continued)

FOREIGN PATENT DOCUMENTS

| | | |
|---|---|---|
| EP | 36061231 A | 2/2020 |
| IN | 201741013738 | 10/2018 |

(Continued)

*Primary Examiner* — Kenneth Bartley
(74) *Attorney, Agent, or Firm* — Miller Johnson

(57) ABSTRACT

A digital health solution system includes: a virtual pharmacy including one or more processors configured to operate a web portal for user devices via a network, the web portal serving as a marketplace for digital health solution applications available for download by and activation on user devices; a digital health marketplace including one or more processors configured to, in response to receipt of user input from a user device: determine activation criteria for a selected one of the digital health solution applications; and transmit the activation criteria to the virtual pharmacy, where the one or more processors of the virtual pharmacy are configured to transmit the activation criteria to the user device via the network; and where the user device is configured to, using the activation criteria, at least one of download and activate the selected one of the digital health solution applications.

40 Claims, 20 Drawing Sheets

(51) Int. Cl.
  *G06Q 30/014* (2023.01)
  *G06Q 30/018* (2023.01)
  *G06Q 30/0203* (2023.01)
  *G06Q 30/0282* (2023.01)
  *G06Q 40/08* (2012.01)
  *G16H 10/20* (2018.01)
  *G16H 10/60* (2018.01)
  *G16H 20/10* (2018.01)
  *G16H 80/00* (2018.01)

(52) U.S. Cl.
  CPC ..... *G06Q 30/0185* (2013.01); *G06Q 30/0203* (2013.01); *G06Q 30/0282* (2013.01); *G06Q 40/08* (2013.01); *G16H 10/20* (2018.01); *G16H 10/60* (2018.01); *G16H 20/10* (2018.01); *G16H 80/00* (2018.01)

(58) Field of Classification Search
  CPC ............... G06Q 30/0282; G06Q 40/08; G06Q 30/0601; G06Q 20/12; G06Q 30/018; G16H 10/60; G16H 20/10; G16H 10/20; G16H 80/00
  See application file for complete search history.

(56) References Cited

U.S. PATENT DOCUMENTS

| | | | |
|---|---|---|---|
| 9,721,231 B2 | 8/2017 | Ruszala | |
| 9,734,287 B2* | 8/2017 | Linn | G16H 40/20 |
| 10,115,087 B2 | 10/2018 | Pourfallah | |
| 10,152,761 B2* | 12/2018 | Kress | G06Q 10/10 |
| 10,346,587 B2 | 7/2019 | Stamper | |
| 10,484,376 B1 | 11/2019 | Laucius | |
| 10,521,778 B2 | 12/2019 | Bull | |
| 10,540,640 B1 | 1/2020 | James | |
| 10,547,594 B2 | 1/2020 | Chang | |
| 11,348,668 B2* | 5/2022 | Atreja | G16H 40/67 |
| 2002/0002495 A1* | 1/2002 | Ullman | G16H 20/10 705/16 |
| 2002/0194081 A1 | 12/2002 | Perkowski | |
| 2005/0022205 A1 | 1/2005 | Green | |
| 2006/0020783 A1 | 1/2006 | Fisher | |
| 2007/0027718 A1 | 2/2007 | Amerantes | |
| 2007/0150480 A1 | 6/2007 | Hwang | |
| 2007/0168228 A1 | 7/2007 | Lawless | |
| 2009/0259493 A1* | 10/2009 | Venon | G16H 20/10 705/3 |
| 2009/0307028 A1 | 12/2009 | Eldon | |
| 2010/0031233 A1 | 2/2010 | Li | |
| 2011/0295614 A1 | 12/2011 | Hummer | |
| 2012/0239560 A1 | 9/2012 | Pourfallah | |
| 2012/0253829 A1* | 10/2012 | John | G16H 40/67 705/2 |
| 2013/0066650 A1* | 3/2013 | Ackerman | G06Q 10/10 705/2 |
| 2013/0166321 A1 | 6/2013 | Harrell | |
| 2013/0204638 A1 | 8/2013 | Lan | |
| 2014/0089836 A1* | 3/2014 | Damani | G16H 70/00 715/771 |
| 2014/0244296 A1* | 8/2014 | Linn | G16H 40/20 705/3 |
| 2014/0278513 A1* | 9/2014 | Prakash | G16H 50/20 705/2 |
| 2014/0379361 A1 | 12/2014 | Mahadkar | |
| 2015/0012283 A1* | 1/2015 | Ryan | G16H 50/50 705/2 |
| 2015/0052009 A1* | 2/2015 | Ketchell, III | G06Q 30/0613 705/26.8 |
| 2015/0100328 A1* | 4/2015 | Kress | G06Q 30/0631 705/2 |
| 2015/0104770 A1* | 4/2015 | Agger | G06Q 10/10 434/236 |
| 2015/0112703 A1* | 4/2015 | Sysko | G16H 20/10 705/2 |
| 2015/0193750 A1 | 7/2015 | Ivanoff | |
| 2015/0193872 A1 | 7/2015 | Ivanoff | |
| 2015/0302154 A1 | 10/2015 | Brooks | |
| 2016/0012194 A1* | 1/2016 | Prakash | G16H 40/40 705/2 |
| 2016/0012465 A1 | 1/2016 | Sharp | |
| 2016/0019354 A1 | 1/2016 | Grant | |
| 2016/0034668 A1 | 2/2016 | Rourke | |
| 2016/0042146 A1* | 2/2016 | Douglass | G16H 50/70 705/3 |
| 2016/0253731 A1 | 9/2016 | Ketchel, III | |
| 2016/0321406 A1* | 11/2016 | Timmerman | G16H 20/10 |
| 2016/0321410 A1* | 11/2016 | Timmerman | G16H 20/10 |
| 2016/0351070 A1* | 12/2016 | Aillon-Sohl | G16H 20/70 |
| 2017/0039324 A1* | 2/2017 | Francois | G16H 10/60 |
| 2017/0147775 A1* | 5/2017 | Ohnemus | G16H 50/50 |
| 2017/0161771 A1* | 6/2017 | Key | G06Q 30/0279 |
| 2017/0213269 A1 | 7/2017 | Setlur | |
| 2017/0220768 A1 | 8/2017 | Tanner, Jr. | |
| 2017/0220782 A1* | 8/2017 | Alsanousi | G16H 80/00 |
| 2017/0351840 A1* | 12/2017 | Goguen | G16H 40/67 |
| 2018/0075430 A1 | 3/2018 | Suzuki | |
| 2018/0082029 A1* | 3/2018 | Bureau | G06Q 30/016 |
| 2018/0108438 A1* | 4/2018 | Ryan | G16H 10/60 |
| 2018/0137247 A1 | 5/2018 | Bore | |
| 2018/0330418 A1 | 11/2018 | Glasgow | |
| 2018/0342007 A1 | 11/2018 | Brannigan | |
| 2018/0344215 A1* | 12/2018 | Ohnemus | A61B 5/1118 |
| 2018/0350451 A1* | 12/2018 | Ohnemus | H04L 67/535 |
| 2019/0026781 A1 | 1/2019 | Beck | |
| 2019/0051388 A1* | 2/2019 | Atreja | G16H 20/10 |
| 2019/0058697 A1 | 2/2019 | Chang | |
| 2019/0065970 A1* | 2/2019 | Bonutti | G06T 7/0012 |
| 2019/0214116 A1* | 7/2019 | Eberting | G16H 40/20 |
| 2019/0304021 A1 | 10/2019 | Rutherford | |
| 2019/0349261 A1 | 11/2019 | Smith | |
| 2019/0355036 A1* | 11/2019 | Ketchel, III | G06Q 30/0629 |
| 2019/0371463 A1* | 12/2019 | Asthana | G06V 10/764 |
| 2019/0374436 A1* | 12/2019 | Townley | G16H 40/63 |
| 2020/0013050 A1 | 1/2020 | Finlow-Bates | |
| 2020/0043070 A1 | 2/2020 | Ketchel, III | |
| 2020/0118127 A1 | 4/2020 | Miller | |
| 2020/0160956 A1 | 5/2020 | Roth | |
| 2020/0257578 A1* | 8/2020 | Creighton | G06F 9/547 |
| 2020/0315531 A1* | 10/2020 | Cooper | A61B 5/0205 |
| 2020/0372993 A1* | 11/2020 | Chu | G16H 20/13 |
| 2020/0387887 A1 | 12/2020 | Rathod | |
| 2022/0007965 A1* | 1/2022 | Tiron | A61B 5/6898 |
| 2022/0246299 A1* | 8/2022 | Gilvert | G16H 40/67 |
| 2022/0383325 A1 | 12/2022 | Hoffman | |
| 2023/0153914 A1 | 5/2023 | Pinsonneault | |

FOREIGN PATENT DOCUMENTS

| | | | |
|---|---|---|---|
| JP | 2005059984 A | 3/2005 | |
| JP | 2019526120 A | 9/2019 | |
| RU | 2725294 C1 * | 6/2020 | |
| TW | 201810151 A | 3/2018 | |
| WO | WO-2016208901 A1 * | 12/2016 | G06F 9/44 |
| WO | 2018126075 A1 | 7/2018 | |
| WO | 2018162687 A1 | 9/2018 | |
| WO | 2018234882 A1 | 12/2018 | |
| WO | 2019036019 A1 | 2/2019 | |
| WO | 2019079890 A1 | 5/2019 | |
| WO | 2019222904 A1 | 11/2019 | |

* cited by examiner

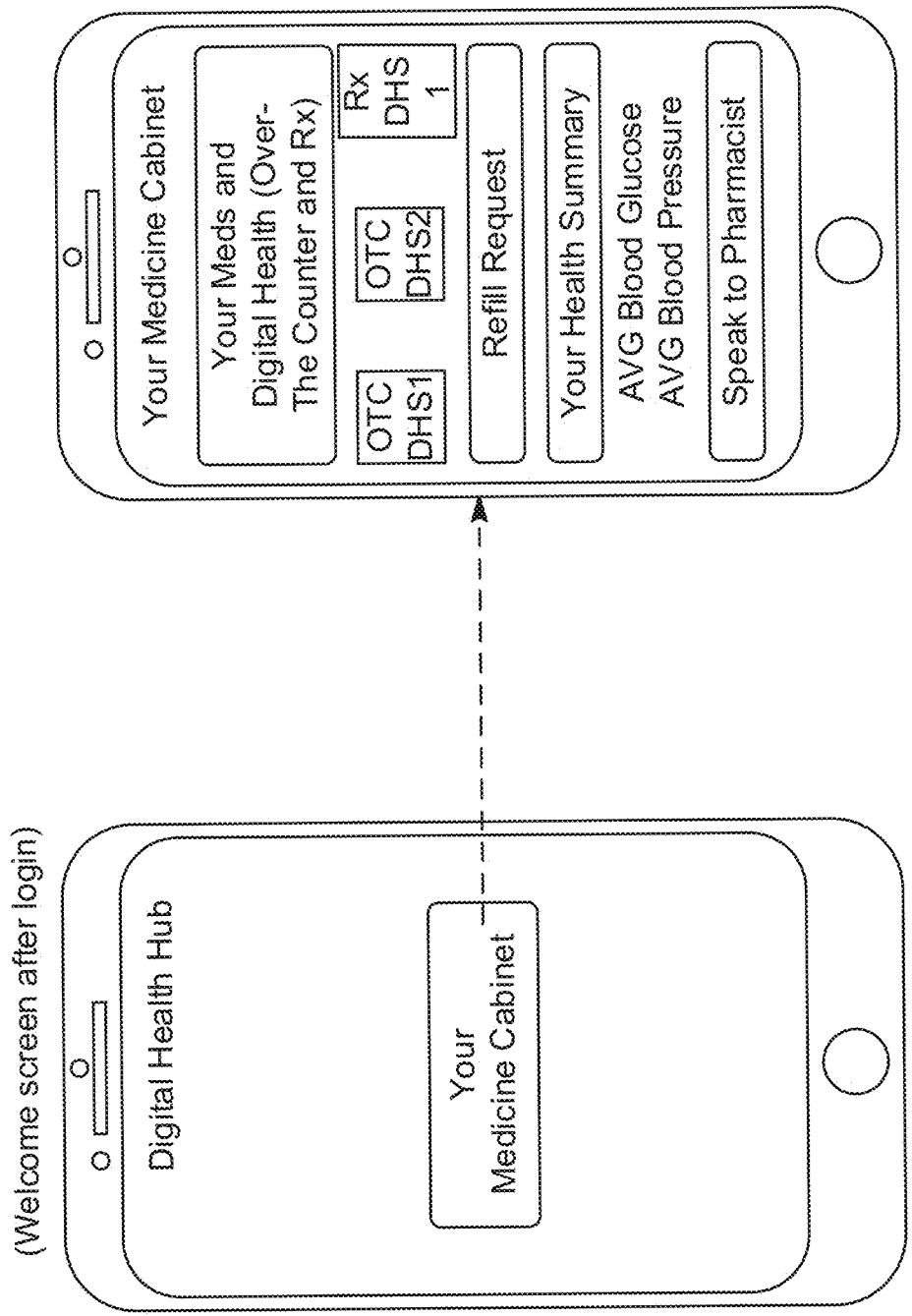

FIG. 7C

- Name
- DOB
- Address
- SSN
- Email
- Phone #
- Benefit Info

FIG. 7B

Health Connect
- Username
- Password

FIG. 7A

Health Connect
- Log In
- Register

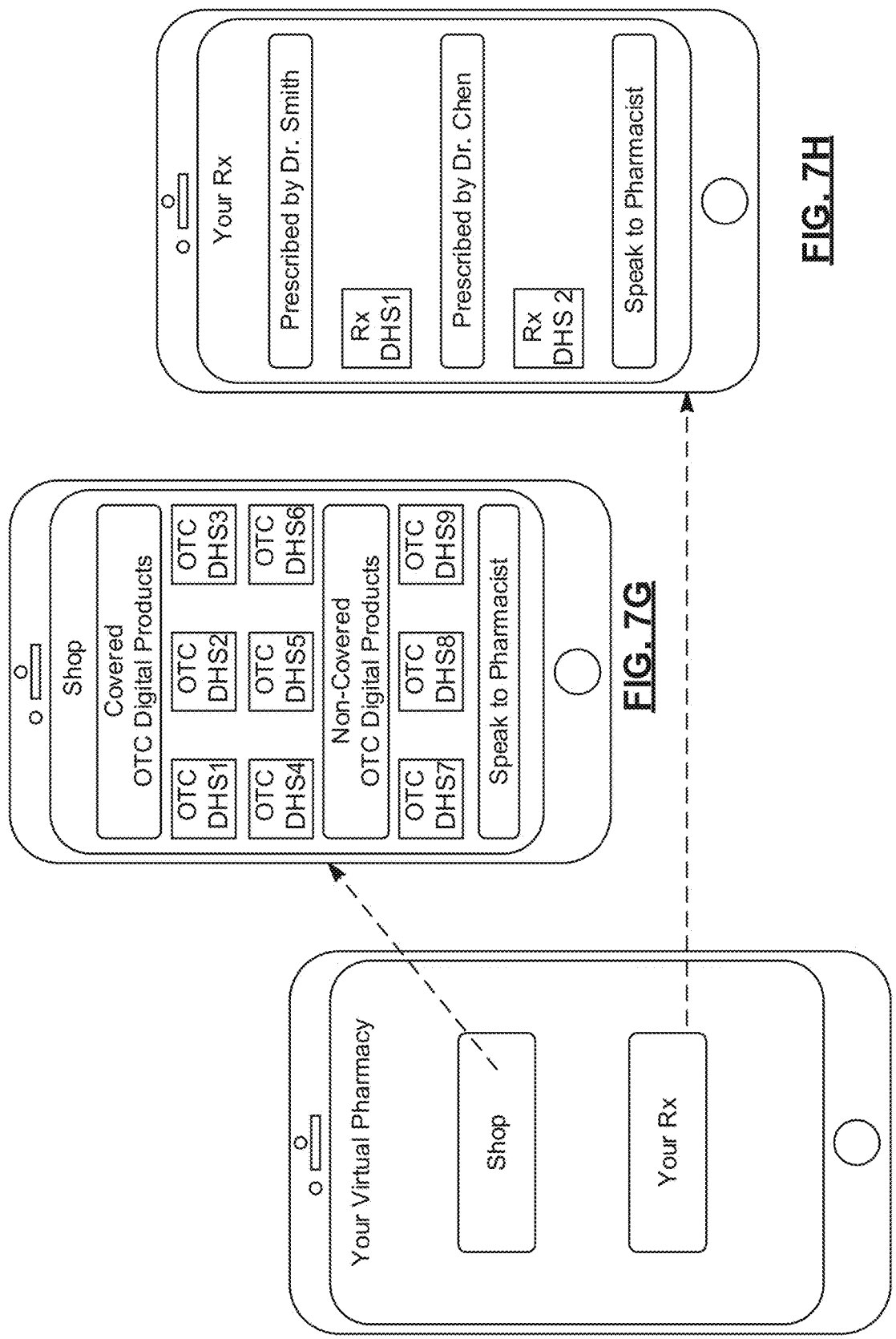

| Health Kit | Google Fit | Samsung Health | Fitbit |

Apple Health Kit

Native iOS Health App That Consolidates Data From Your iPhone, Apple Watch, and Third-Party Apps Connect Apple Health Kit

Google Fit

Native Android Health-Tracking Platform That Blends Data from Multiple Apps and Devices.

Connect Google Fit

Samsung Health

A Free App That Tracks Various Things Such as Physical Activity, Diet, and Sleep.

Connect Samsung Health

| Apple Watch | Samsung Galaxy Watch | Polar Watch | OURA |

Apple Watch

Connect Your Apple Watch to Sync Your Activity Data.

Connect Your Apple Watch

Samsung Galaxy Watch

Connect Your Samsung Galaxy Watch to Sync Your Activity Data.

Connect Your Samsung Galaxy Watch

Polar Watch

Connect Your Polar Watch to Sync Your Activity Data.

Connect Your Polar Watch

Other Wearables

Connect Your Health Devices & Share Daily Health Matrix so we can Serve You Better Connect Your Devices

Sleep Number 360 Smart Bed

Connect Your 360 Smart Bed to Sync Your Sleep Data.

Connect Your 360 Smart Bed

Eight Sleep Smart Bed

Connect Your Eight Sleep Smart Bed to Sync Your Sleep Data.

Connect Your Eight Sleep Smart Bed

Samsung Family Hub Smart Fridge

Connect Your Smart Fridge to Sync Your Eating Data.

Connect Your Samsung Family Hub

Other Smart Fridges

Connect Your Smart Fridge so we can Serve You Better.

Connect Your Smart Fridge

FIG. 9

Diabetes 1

OneTouch Diabetes Remote Monitoring

Insulin Delivery, at any Time From up to 10 Feet Away With OneTouch™

View System

Diabetes 2

Livongo Diabetes Insight

Using Personalized Health Insights to Treat Diabetes and Hypertension

View Tool

Sleep

Sleep Program

A Digital Sleep-Improvement Program Featuring Cognitive Behavioral Therapy (CBT)Techniques.

Improve Sleep

Therapeutic Resource Centers

Therapy Management Program for Treating These Rare Complex Diseases

Sign Up

Therapease Cuisine

Nutritional Services Program for Those Diagnosed With Cancer.

Sign Up

Community Resources

Connect With People Who Share Similar Health Condition as Yours.

Explore Communities

Health Tools

Connect Your Health Devices & Share Daily Health Matrix so we can Serve You Better Connect Your Devices

FIG. 11

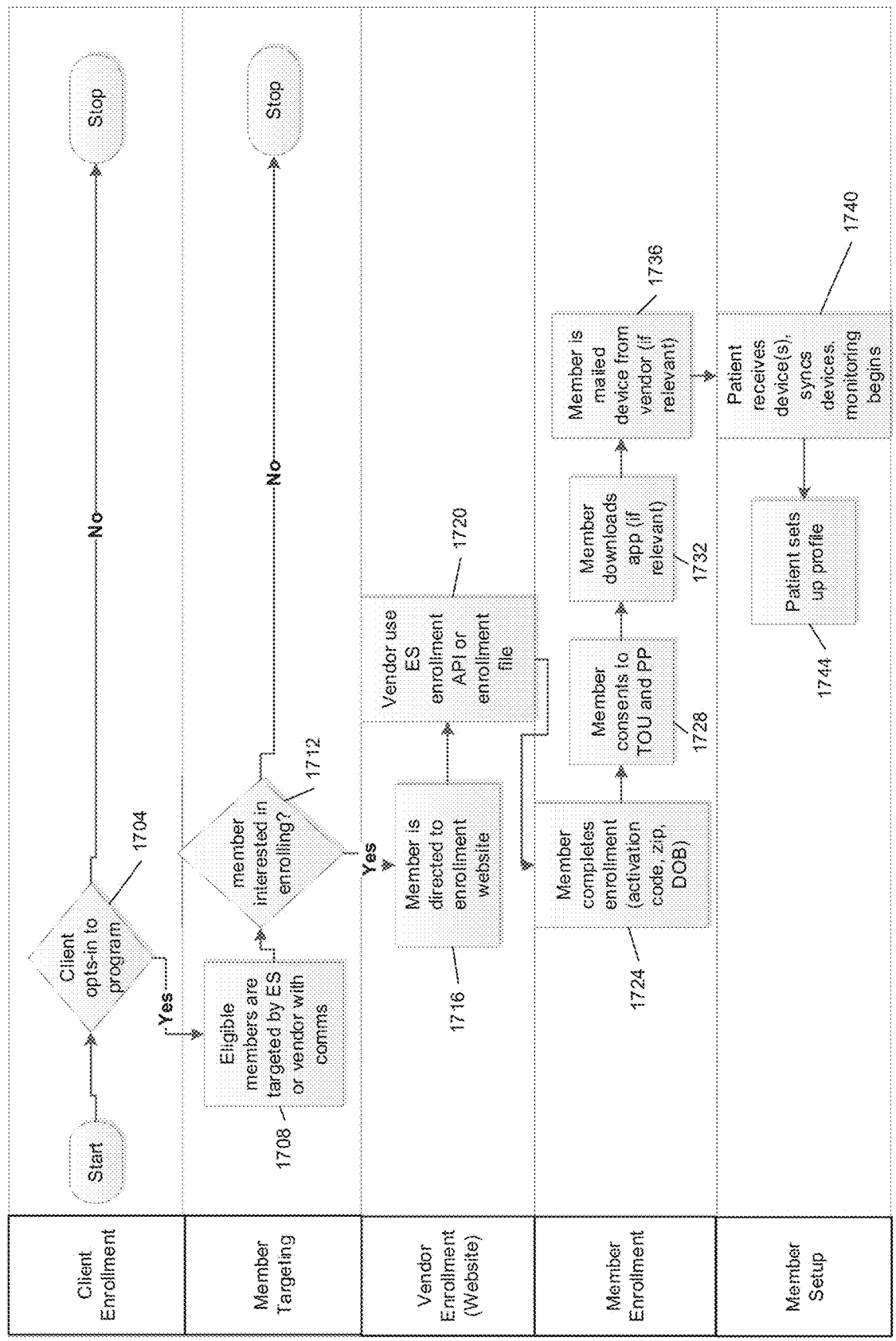

COMPUTERIZED AGGREGATION AND DISTRIBUTION ARCHITECTURE FOR DIGITAL HEALTH INFRASTRUCTURE

CROSS-REFERENCE TO RELATED APPLICATIONS

This application claims the benefit of U.S. Provisional Application No. 62/848,543, filed May 15, 2019. The entire disclosure of the application referenced above is incorporated by reference.

FIELD

The present disclosure relates to computerized health interventions and therapeutics and more particularly to distribution platforms for computerized health interventions and therapeutics.

BACKGROUND

Therapies for patients may take the form of medications, such as pills, whether prescribed by a clinician or obtained by the patient over-the-counter. Recently, digital therapies and digital interventions have become available to supplement the effectiveness of and adherence to medications, to gather medical data, and to treat patients directly.

In fact, there are by some estimates over 318,000 health-related applications (apps) available currently. This makes evaluating the safety and efficacy of apps by interested parties, such as pharmacy benefit managers, very difficult and makes it nearly impossible for an individual patient to identify the best app or apps for their needs.

The background description provided here is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

In a feature, a digital health solution system includes: a virtual pharmacy comprising one or more processors configured to operate a web portal for user devices via a network, the web portal serving as a marketplace for digital health solution applications that are available for download by and activation on user devices, where the web portal is navigable to via applications installed on the user devices; a digital health marketplace including one or more processors configured to, in response to receipt of user input from a user device indicative of a selection of one of the digital health solution applications for download and activation: determine activation criteria for the one of the digital health solution applications; and transmit the activation criteria to the virtual pharmacy, where the one or more processors of the virtual pharmacy are configured to transmit the activation criteria to the user device via the network; and where the user device is configured to, using the activation criteria, at least one of download and activate the one of the digital health solution applications.

In further features, the activation criteria includes an activation token, and the one or more processors of the digital health marketplace are configured to obtain the activation token from a developer computer of a developer of the one of the digital health solution applications.

In further features, the activation criteria includes an activation token, and the digital health marketplace is configured to select the activation token from a set of activation tokens that are cached at the digital health marketplace.

In further features, the activation criteria includes an activation code for activating the one of the digital health solution applications after downloading.

In further features, the activation criteria includes a link to a digital distribution platform for downloading the one of the digital health solution applications.

In further features, the link includes a uniform resource locator (URL).

In further features: the one or more processors of the digital health marketplace are configured to determine scores for the digital health solution applications, respectively; and the one or more processors of the virtual pharmacy are configured to output the scores for the digital health solution applications, respectively, via the web portal.

In further features, the one or more processors of the digital health marketplace are configured to determine the scores for the digital health solution applications, respectively, based on at least one of usability of the digital health solution applications, technical scalability of the digital health solution applications, security of the digital health solution applications, adoption of the digital health solution applications, and empirical result data for the digital health solution applications.

In further features, the one or more processors of the virtual pharmacy are configured to output a tiered ranking of the digital health solution applications based on at least one of: the scores of the digital health solution applications, respectively; and clinical criteria and health benefit plan coverage.

In further features, the one or more processors of the digital health marketplace are configured to selectively add ones of the digital health solution applications to the web portal.

In further features, the one or more processors of the digital health marketplace are configured to determine whether to add ones of the digital health solution applications to the web portal based on at least one of clinical components of the digital health solution applications, usability components of the digital health solution applications, and values of the digital health solution applications, respectively.

In further features, the one or more processors of the digital health marketplace are configured to determine the values of the digital health solution applications based on returns on investment of the digital health solution applications, respectively.

In further features, the one or more processors of the digital health marketplace are configured to determine the returns on investment of the digital health solution applications based on efficacy models of the digital health solution applications and pricing models of the digital health solution applications, respectively.

In further features, the pricing models include at least one of per-person per-month costs and volume discounts.

In further features, a benefit manager includes one or more processors configured to determine a portion of a first cost of the one of the digital health solution applications covered by a health benefit plan of a user of the user device based on an identity of the user, where the one or more processors of the digital health marketplace are configured to output a final cost of the one of the digital health solution applications to the user device based on the portion of the first cost.

In further features, the one or more processors of the benefit manager are configured to determine recommendations of ones of the digital health solution applications that are relevant to a user and to transmit the recommendations to a physician computer of a physician of the user.

In further features, the benefit manager is configured to determine the recommendations using an interface developed based on Fast Healthcare Interoperability Resources (FHIR).

In further features, the activation criteria is included in an electronic prescription received from an electronic health record (EHR) system for the one of the digital health solution applications.

In further features, the one or more processors of the virtual pharmacy are configured to transmit a notification to the user device in response to receipt of the electronic prescription for the one of the digital health solution applications.

In further features, the notification includes at least one of a text message, a short message service (SMS) message, an email, a smartphone notification, an automated voice call, and a personal voice call.

In further features, the activation criteria is included on a prescription printed on paper.

In further features, the prescription printed on paper includes at least one of a uniform resource locator (URL) and a quick response (QR) code.

In further features, the digital health solution applications include non-generic branded digital health solution applications and generic branded digital health solution applications.

In further features, the one or more 2 of the virtual pharmacy are configured to receive reviews of the digital health solution applications from user devices and to provide review information to the virtual pharmacy based on the reviews.

In further features, the one or more processors of the virtual pharmacy are configured to output usage data the digital health solution applications to the user devices via the web portal.

In further features, the usage data includes at least one of an average number of monthly users, a total number of lifetime users, and monthly retention percentages.

In further features, the one or more processors of the virtual pharmacy are configured to, in response to not receiving any prescriptions for the user of the user device: output a set of questions to the user device the user via the network; receive answers to the questions from the user device via the network; determine a recommendation for one or more of the digital health solution applications based on the answers; and output the recommendation to the user device via the network.

In further features, the one or more processors of the virtual pharmacy are configured to determine the set of questions using at least one of a decision tree and a decision table.

In further features, the virtual pharmacy includes a recommendation engine configured to receive the answers as inputs and generate the recommendation as an output.

In further features, the recommendation includes indicators of whether the one or more of the digital health solution applications are covered for the user under a health benefit plan of the user.

In further features, the one or more processors of the virtual pharmacy are configured to rank the one or more of the digital health solution applications in the recommendation based on at least one of health benefit plan coverage, pricing, and information from the digital health marketplace.

In further features, the information from the digital health marketplace includes at least one of user feedback, social media impressions, and adoption rate.

In further features, the virtual pharmacy is configured to, in response to user input, filter the digital health solution applications by at least one of category, symptoms, disease state, health benefit plan coverage, and price.

In further features, the user device is configured to download the one of the digital health solution applications from a digital distribution platform.

In further features, the user device is configured to download the one of the digital health solution applications from a developer computer of a developer of the one of the digital health solution applications.

In further features, a developer computer of a developer of the one of the digital health solution applications includes one or more processors configured to: collect usage data for the one of the digital health solution applications from the user device after downloading; and selectively transmit the collected usage data to at least one of the virtual pharmacy and the digital health marketplace.

In further features, the usage data includes at least one of a frequency of use of the one of the digital health solution applications and a length of use of the one of the digital health solution applications.

In further features, the one or more processors of the digital health marketplace are further configured to selectively recall one of the digital health solution applications from the virtual pharmacy, thereby rendering the recalled one of the digital health solution applications unavailable for at least one of downloading and activation via the virtual pharmacy.

In a feature, a digital health solution system includes: a virtual pharmacy comprising one or more processors configured to operate a web portal for user devices via a network, the web portal serving as a marketplace for digital health solution applications that are available for download by and activation on user devices, where the web portal is navigable to via applications installed on the user devices; and a digital health marketplace including one or more processors configured to communicate with developer computers of developers of the digital health solution applications, where the one or more processors of the virtual pharmacy are configured to, in response to receipt of user input from a user device indicative of a selection of one of the digital health solution applications, obtain activation criteria from the user device and transmit the activation criteria to the digital health marketplace, where the one or more processors of the digital health marketplace are configured to transmit the activation criteria to a developer computer of a developer of the one of the digital health solution applications, and where the developer computer is configured to allow the user device to download the one of the digital health solution applications in response to receipt of the activation criteria.

In further features, the activation criteria includes one of a phone number of the user device and an email address of a user of the user device.

In a feature, a method of distributing digital health solution applications includes: by a virtual pharmacy comprising one or more processors, operating a web portal for user devices via a network, the web portal serving as a marketplace for digital health solution applications that are available for download by and activation on user devices, where the web portal is navigable to via applications installed on the user devices; by a digital health marketplace comprising one or more processors, in response to receipt of user input from a user device indicative of a selection of one of the digital health solution applications for download and activation: determining activation criteria for the one of the digital health solution applications; and transmitting the activation criteria to the virtual pharmacy; by the one or more processors of the virtual pharmacy, transmitting the activation criteria to the user device via the network; and by the user device, using the activation criteria, at least one of downloading and activating the one of the digital health solution applications.

In a feature, a method of distributing digital health solution applications includes: by a virtual pharmacy comprising one or more processors, operating a web portal for user devices via a network, the web portal serving as a marketplace for digital health solution applications that are available for download by and activation on user devices, where the web portal is navigable to via applications installed on the user devices; by a digital health marketplace including one or more processors, communicating with developer computers of developers of the digital health solution applications; by the one or more processors of the virtual pharmacy, in response to receipt of user input from a user device indicative of a selection of one of the digital health solution applications, obtaining activation criteria from the user device and transmitting the activation criteria to the digital health marketplace; by the one or more processors of the digital health marketplace, transmitting the activation criteria to a developer computer of a developer of the one of the digital health solution applications; and by the developer computer, allowing the user device to download the one of the digital health solution applications in response to receipt of the activation criteria.

In further features, the concepts of above paragraphs can be added to the concepts of the preceding paragraphs in various combinations.

Further areas of applicability of the present disclosure will become apparent from the detailed description, the claims, and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings.

FIGS. 6A-6E are graphical representations of example smartphone user interfaces for a digital health hub user interface.

FIGS. 7A-7H are graphical representations of example smartphone user interfaces for a health connect user interface.

FIGS. 9-11 are example smartphone user interfaces.

FIGS. 12-17 are flowcharts depicting examples of managing member communications, member enrollments, and control of digital pharmacy products.

In the drawings, reference numbers may be reused to identify similar and/or identical elements.

DETAILED DESCRIPTION

High-Volume Pharmacy

Figure 1:
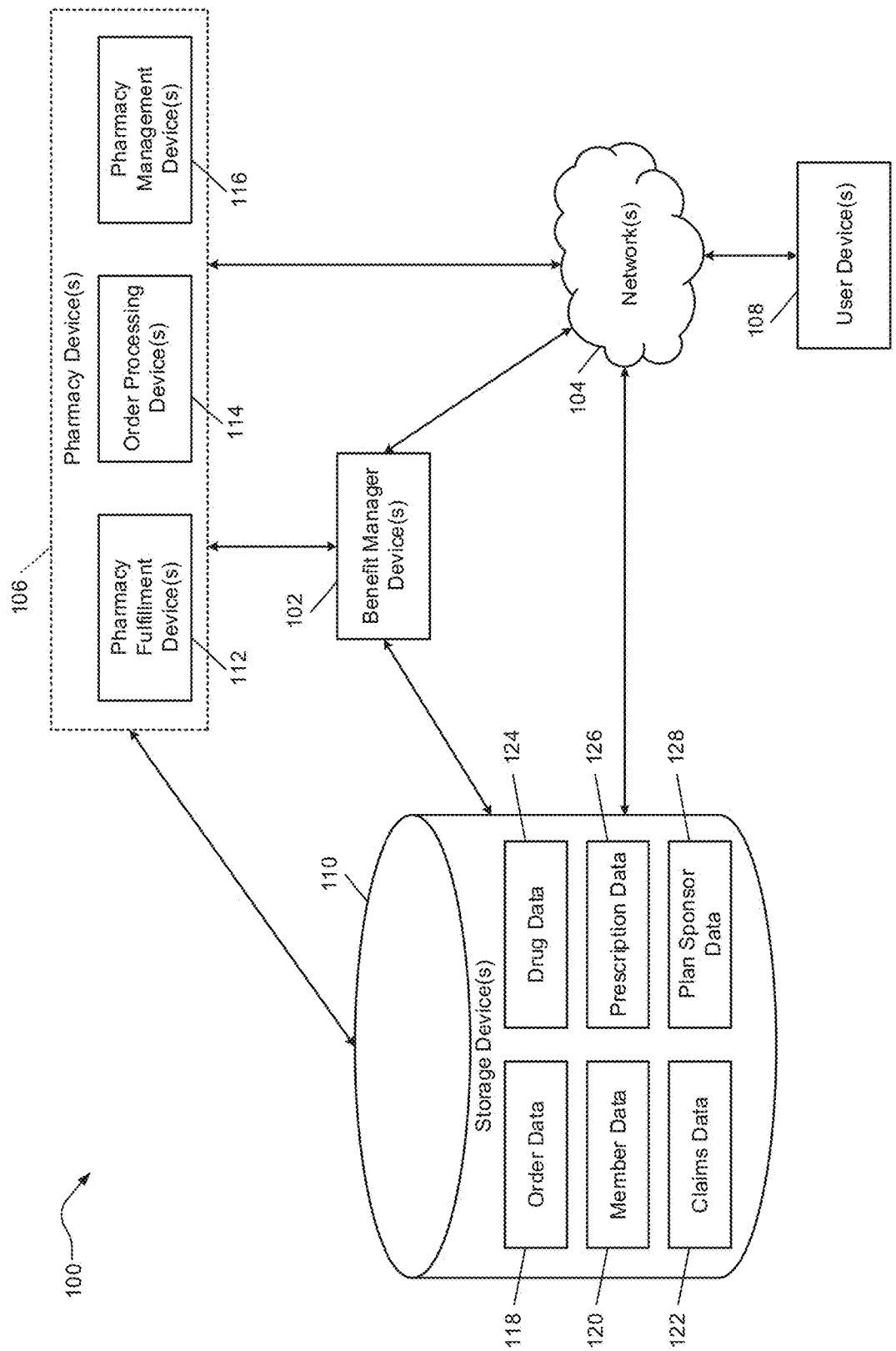
FIG. 1 is a functional block diagram of an example system including a high-volume pharmacy.

FIG. 1 is a block diagram of an example implementation of a system 100 for a high-volume pharmacy. While the system 100 is generally described as being deployed in a high-volume pharmacy or a fulfillment center (for example, a mail order pharmacy, a direct delivery pharmacy, etc.), the system 100 and/or components of the system 100 may otherwise be deployed (for example, in a lower-volume pharmacy, etc.). A high-volume pharmacy may be a pharmacy that is capable of filling at least some prescriptions mechanically. The system 100 may include a benefit manager device 102 and a pharmacy device 106 in communication with each other directly and/or over a network 104.

The system 100 may also include one or more user device(s) 108. A user, such as a pharmacist, patient, data analyst, health plan administrator, etc., may access the benefit manager device 102 or the pharmacy device 106 using the user device 108. The user device 108 may be a desktop computer, a laptop computer, a tablet, a smartphone, etc.

The benefit manager device 102 is a device operated by an entity that is at least partially responsible for creation and/or management of the pharmacy or drug benefit. While the entity operating the benefit manager device 102 is typically a pharmacy benefit manager (PBM), other entities may operate the benefit manager device 102 on behalf of themselves or other entities (such as PBMs). For example, the benefit manager device 102 may be operated by a health plan, a retail pharmacy chain, a drug wholesaler, a data analytics or other type of software-related company, etc. In some implementations, a PBM that provides the pharmacy benefit may provide one or more additional benefits including a medical or health benefit, a dental benefit, a vision benefit, a wellness benefit, a radiology benefit, a pet care benefit, an insurance benefit, a long term care benefit, a nursing home benefit, etc. The PBM may, in addition to its PBM operations, operate one or more pharmacies. The pharmacies may be retail pharmacies, mail order pharmacies, etc.

Some of the operations of the PBM that operates the benefit manager device 102 may include the following activities and processes. A member (or a person on behalf of the member) of a pharmacy benefit plan may obtain a prescription drug at a retail pharmacy location (e.g., a location of a physical store) from a pharmacist or a pharmacist technician. The member may also obtain the prescription drug through mail order drug delivery from a mail order pharmacy location, such as the system 100. In some implementations, the member may obtain the prescription drug directly or indirectly through the use of a machine, such as a kiosk, a vending unit, a mobile electronic device, or a different type of mechanical device, electrical device, electronic communication device, and/or computing device. Such a machine may be filled with the prescription drug in prescription packaging, which may include multiple prescription components, by the system 100. The pharmacy benefit plan is administered by or through the benefit manager device 102.

The member may have a copayment for the prescription drug that reflects an amount of money that the member is responsible to pay the pharmacy for the prescription drug. The money paid by the member to the pharmacy may come from, as examples, personal funds of the member, a health savings account (HSA) of the member or the member's family, a health reimbursement arrangement (HRA) of the member or the member's family, or a flexible spending account (FSA) of the member or the member's family. In some instances, an employer of the member may directly or indirectly fund or reimburse the member for the copayments.

The amount of the copayment required by the member may vary across different pharmacy benefit plans having different plan sponsors or clients and/or for different prescription drugs. The member's copayment may be a flat copayment (in one example, $10), coinsurance (in one example, 10%), and/or a deductible (for example, responsibility for the first $500 of annual prescription drug expense, etc.) for certain prescription drugs, certain types and/or classes of prescription drugs, and/or all prescription drugs. The copayment may be stored in a storage device 110 or determined by the benefit manager device 102.

In some instances, the member may not pay the copayment or may only pay a portion of the copayment for the prescription drug. For example, if a usual and customary cost for a generic version of a prescription drug is $4, and the member's flat copayment is $20 for the prescription drug, the member may only need to pay $4 to receive the prescription drug. In another example involving a worker's compensation claim, no copayment may be due by the member for the prescription drug.

In addition, copayments may also vary based on different delivery channels for the prescription drug. For example, the copayment for receiving the prescription drug from a mail order pharmacy location may be less than the copayment for receiving the prescription drug from a retail pharmacy location.

In conjunction with receiving a copayment (if any) from the member and dispensing the prescription drug to the member, the pharmacy submits a claim to the PBM for the prescription drug. After receiving the claim, the PBM (such as by using the benefit manager device 102) may perform certain adjudication operations including verifying eligibility for the member, identifying/reviewing an applicable formulary for the member to determine any appropriate copayment, coinsurance, and deductible for the prescription drug, and performing a drug utilization review (DUR) for the member. Further, the PBM may provide a response to the pharmacy (for example, the pharmacy system 100) following performance of at least some of the aforementioned operations.

As part of the adjudication, a plan sponsor (or the PBM on behalf of the plan sponsor) ultimately reimburses the pharmacy for filling the prescription drug when the prescription drug was successfully adjudicated. The aforementioned adjudication operations generally occur before the copayment is received and the prescription drug is dispensed. However in some instances, these operations may occur simultaneously, substantially simultaneously, or in a different order. In addition, more or fewer adjudication operations may be performed as at least part of the adjudication process.

The amount of reimbursement paid to the pharmacy by a plan sponsor and/or money paid by the member may be determined at least partially based on types of pharmacy networks in which the pharmacy is included. In some implementations, the amount may also be determined based on other factors. For example, if the member pays the pharmacy for the prescription drug without using the prescription or drug benefit provided by the PBM, the amount of money paid by the member may be higher than when the member uses the prescription or drug benefit. In some implementations, the amount of money received by the pharmacy for dispensing the prescription drug and for the prescription drug itself may be higher than when the member uses the prescription or drug benefit. Some or all of the foregoing operations may be performed by executing instructions stored in the benefit manager device 102 and/or an additional device.

Examples of the network 104 include a Global System for Mobile Communications (GSM) network, a code division multiple access (CDMA) network, 3rd Generation Partnership Project (3GPP), an Internet Protocol (IP) network, a Wireless Application Protocol (WAP) network, or an IEEE 802.11 standards network, as well as various combinations of the above networks. The network 104 may include an optical network. The network 104 may be a local area network or a global communication network, such as the Internet. In some implementations, the network 104 may include a network dedicated to prescription orders: a prescribing network such as the electronic prescribing network operated by Surescripts of Arlington, Virginia.

Moreover, although the system shows a single network 104, multiple networks can be used. The multiple networks may communicate in series and/or parallel with each other to link the devices 102-110.

The pharmacy device 106 may be a device associated with a retail pharmacy location (e.g., an exclusive pharmacy location, a grocery store with a retail pharmacy, or a general sales store with a retail pharmacy) or other type of pharmacy location at which a member attempts to obtain a prescription. The pharmacy may use the pharmacy device 106 to submit the claim to the PBM for adjudication.

Additionally, in some implementations, the pharmacy device 106 may enable information exchange between the pharmacy and the PBM. For example, this may allow the sharing of member information such as drug history that may allow the pharmacy to better service a member (for example, by providing more informed therapy consultation and drug interaction information). In some implementations, the benefit manager device 102 may track prescription drug fulfillment and/or other information for users that are not members, or have not identified themselves as members, at the time (or in conjunction with the time) in which they seek to have a prescription filled at a pharmacy.

The pharmacy device 106 may include a pharmacy fulfillment device 112, an order processing device 114, and a pharmacy management device 116 in communication with each other directly and/or over the network 104. The order processing device 114 may receive information regarding filling prescriptions and may direct an order component to one or more devices of the pharmacy fulfillment device 112 at a pharmacy. The pharmacy fulfillment device 112 may fulfill, dispense, aggregate, and/or pack the order components of the prescription drugs in accordance with one or more prescription orders directed by the order processing device 114.

In general, the order processing device 114 is a device located within or otherwise associated with the pharmacy to enable the pharmacy fulfilment device 112 to fulfill a prescription and dispense prescription drugs. In some implementations, the order processing device 114 may be an external order processing device separate from the pharmacy and in communication with other devices located within the pharmacy.

For example, the external order processing device may communicate with an internal pharmacy order processing device and/or other devices located within the system 100. In some implementations, the external order processing device may have limited functionality (e.g., as operated by a user requesting fulfillment of a prescription drug), while the internal pharmacy order processing device may have greater functionality (e.g., as operated by a pharmacist).

The order processing device 114 may track the prescription order as it is fulfilled by the pharmacy fulfillment device 112. The prescription order may include one or more prescription drugs to be filled by the pharmacy. The order processing device 114 may make pharmacy routing decisions and/or order consolidation decisions for the particular prescription order. The pharmacy routing decisions include what device(s) in the pharmacy are responsible for filling or otherwise handling certain portions of the prescription order. The order consolidation decisions include whether portions of one prescription order or multiple prescription orders should be shipped together for a user or a user family. The order processing device 114 may also track and/or schedule literature or paperwork associated with each prescription order or multiple prescription orders that are being shipped together. In some implementations, the order processing device 114 may operate in combination with the pharmacy management device 116.

The order processing device 114 may include circuitry, a processor, a memory to store data and instructions, and communication functionality. The order processing device 114 is dedicated to performing processes, methods, and/or instructions described in this application. Other types of electronic devices may also be used that are specifically configured to implement the processes, methods, and/or instructions described in further detail below.

In some implementations, at least some functionality of the order processing device 114 may be included in the pharmacy management device 116. The order processing device 114 may be in a client-server relationship with the pharmacy management device 116, in a peer-to-peer relationship with the pharmacy management device 116, or in a different type of relationship with the pharmacy management device 116. The order processing device 114 and/or the pharmacy management device 116 may communicate directly (for example, such as by using a local storage) and/or through the network 104 (such as by using a cloud storage configuration, software as a service, etc.) with the storage device 110.

The storage device 110 may include: non-transitory storage (for example, memory, hard disk, CD-ROM, etc.) in communication with the benefit manager device 102 and/or the pharmacy device 106 directly and/or over the network 104. The non-transitory storage may store order data 118, member data 120, claims data 122, drug data 124, prescription data 126, and/or plan sponsor data 128. Further, the system 100 may include additional devices, which may communicate with each other directly or over the network 104.

The order data 118 may be related to a prescription order. The order data may include type of the prescription drug (for example, drug name and strength) and quantity of the prescription drug. The order data 118 may also include data used for completion of the prescription, such as prescription materials. In general, prescription materials include an electronic copy of information regarding the prescription drug for inclusion with or otherwise in conjunction with the fulfilled prescription. The prescription materials may include electronic information regarding drug interaction warnings, recommended usage, possible side effects, expiration date, date of prescribing, etc. The order data 118 may be used by a high-volume fulfillment center to fulfill a pharmacy order.

In some implementations, the order data 118 includes verification information associated with fulfillment of the prescription in the pharmacy. For example, the order data 118 may include videos and/or images taken of (i) the prescription drug prior to dispensing, during dispensing, and/or after dispensing, (ii) the prescription container (for example, a prescription container and sealing lid, prescription packaging, etc.) used to contain the prescription drug prior to dispensing, during dispensing, and/or after dispensing, (iii) the packaging and/or packaging materials used to ship or otherwise deliver the prescription drug prior to dispensing, during dispensing, and/or after dispensing, and/or (iv) the fulfillment process within the pharmacy. Other types of verification information such as barcode data read from pallets, bins, trays, or carts used to transport prescriptions within the pharmacy may also be stored as order data 118.

The member data 120 includes information regarding the members associated with the PBM. The information stored as member data 120 may include personal information, personal health information, protected health information, etc. Examples of the member data 120 include name, address, telephone number, e-mail address, prescription drug history, etc. The member data 120 may include a plan sponsor identifier that identifies the plan sponsor associated with the member and/or a member identifier that identifies the member to the plan sponsor. The member data 120 may include a member identifier that identifies the plan sponsor associated with the user and/or a user identifier that identifies the user to the plan sponsor. The member data 120 may also include dispensation preferences such as type of label, type of cap, message preferences, language preferences, etc.

The member data 120 may be accessed by various devices in the pharmacy (for example, the high-volume fulfillment center, etc.) to obtain information used for fulfillment and shipping of prescription orders. In some implementations, an external order processing device operated by or on behalf of a member may have access to at least a portion of the member data 120 for review, verification, or other purposes.

In some implementations, the member data 120 may include information for persons who are users of the pharmacy but are not members in the pharmacy benefit plan being provided by the PBM. For example, these users may obtain drugs directly from the pharmacy, through a private label service offered by the pharmacy, the high-volume fulfillment center, or otherwise. In general, the terms "member" and "user" may be used interchangeably.

The claims data 122 includes information regarding pharmacy claims adjudicated by the PBM under a drug benefit program provided by the PBM for one or more plan sponsors. In general, the claims data 122 includes an identification of the client that sponsors the drug benefit program under which the claim is made, and/or the member that purchased the prescription drug giving rise to the claim, the prescription drug that was filled by the pharmacy (e.g., the national drug code number, etc.), the dispensing date, generic indicator, generic product identifier (GPI) number, medication class, the cost of the prescription drug provided under the drug benefit program, the copayment/coinsurance amount, rebate information, and/or member eligibility, etc. Additional information may be included.

In some implementations, other types of claims beyond prescription drug claims may be stored in the claims data 122. For example, medical claims, dental claims, wellness claims, or other types of health-care-related claims for members may be stored as a portion of the claims data 122.

In some implementations, the claims data 122 includes claims that identify the members with whom the claims are associated. Additionally or alternatively, the claims data 122 may include claims that have been de-identified (that is, associated with a unique identifier but not with a particular, identifiable member).

The drug data 124 may include drug name (e.g., technical name and/or common name), other names by which the drug is known, active ingredients, an image of the drug (such as in pill form), etc. The drug data 124 may include information associated with a single medication or multiple medications.

The prescription data 126 may include information regarding prescriptions that may be issued by prescribers on behalf of users, who may be members of the pharmacy benefit plan—for example, to be filled by a pharmacy. Examples of the prescription data 126 include user names, medication or treatment (such as lab tests), dosing information, etc. The prescriptions may include electronic prescriptions or paper prescriptions that have been scanned. In some implementations, the dosing information reflects a frequency of use (e.g., once a day, twice a day, before each meal, etc.) and a duration of use (e.g., a few days, a week, a few weeks, a month, etc.).

In some implementations, the order data 118 may be linked to associated member data 120, claims data 122, drug data 124, and/or prescription data 126.

The plan sponsor data 128 includes information regarding the plan sponsors of the PBM. Examples of the plan sponsor data 128 include company name, company address, contact name, contact telephone number, contact e-mail address, etc.

Figure 2:
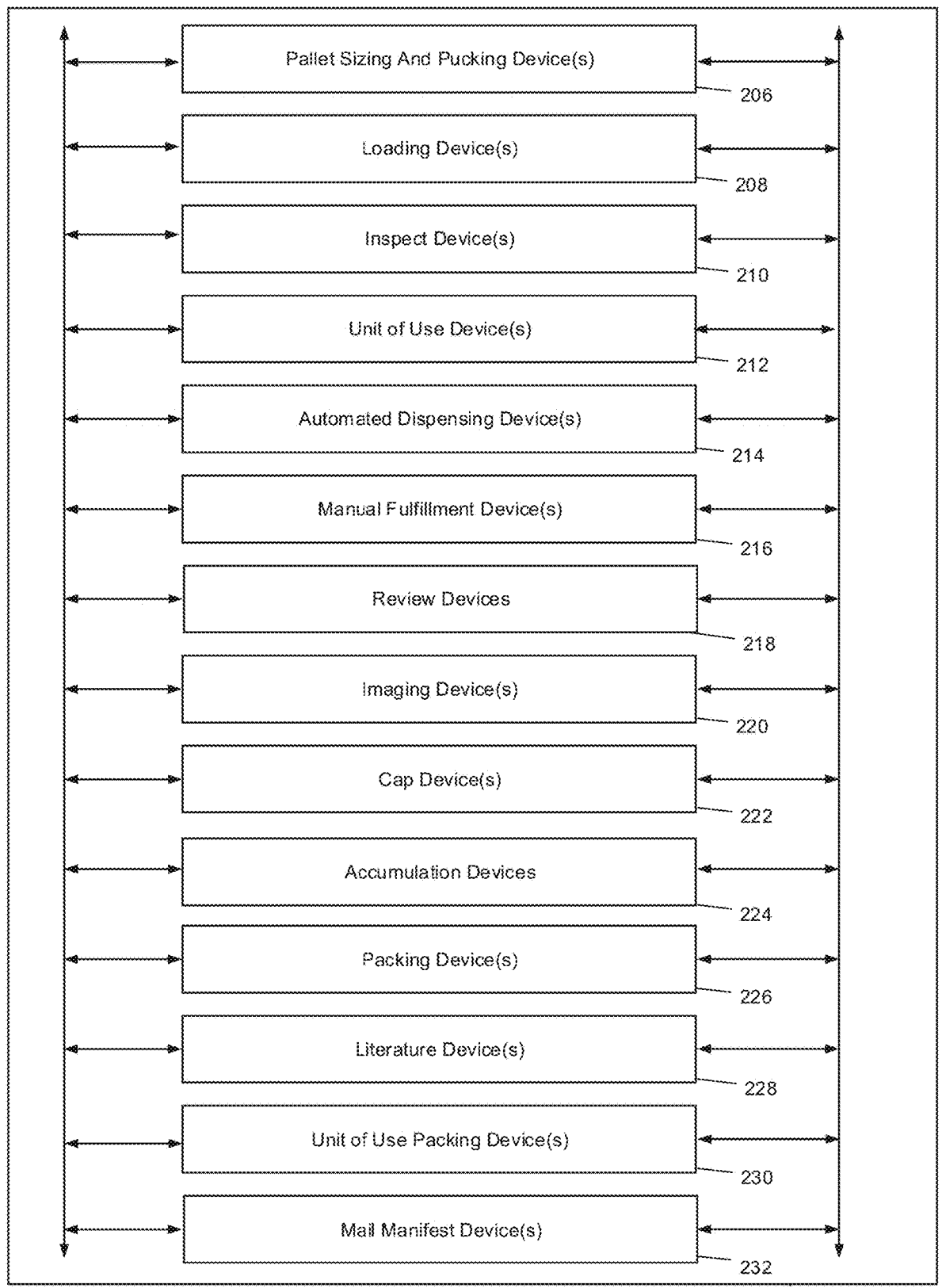
FIG. 2 is a functional block diagram of an example pharmacy fulfillment device, which may be deployed within the system of FIG. 1.

FIG. 2 illustrates the pharmacy fulfillment device 112 according to an example implementation. The pharmacy fulfillment device 112 may be used to process and fulfill prescriptions and prescription orders. After fulfillment, the fulfilled prescriptions are packed for shipping.

The pharmacy fulfillment device 112 may include devices in communication with the benefit manager device 102, the order processing device 114, and/or the storage device 110, directly or over the network 104. Specifically, the pharmacy fulfillment device 112 may include pallet sizing and pucking device(s) 206, loading device(s) 208, inspect device(s) 210, unit of use device(s) 212, automated dispensing device(s) 214, manual fulfillment device(s) 216, review devices 218, imaging device(s) 220, cap device(s) 222, accumulation devices 224, packing device(s) 226, literature device(s) 228, unit of use packing device(s) 230, and mail manifest device (s) 232. Further, the pharmacy fulfillment device 112 may include additional devices, which may communicate with each other directly or over the network 104.

In some implementations, operations performed by one of these devices 206-232 may be performed sequentially, or in parallel with the operations of another device as may be coordinated by the order processing device 114. In some implementations, the order processing device 114 tracks a prescription with the pharmacy based on operations performed by one or more of the devices 206-232.

In some implementations, the pharmacy fulfillment device 112 may transport prescription drug containers, for example, among the devices 206-232 in the high-volume fulfillment center, by use of pallets. The pallet sizing and pucking device 206 may configure pucks in a pallet. A pallet may be a transport structure for a number of prescription containers, and may include a number of cavities. A puck may be placed in one or more than one of the cavities in a pallet by the pallet sizing and pucking device 206. The puck may include a receptacle sized and shaped to receive a prescription container. Such containers may be supported by the pucks during carriage in the pallet. Different pucks may have differently sized and shaped receptacles to accommodate containers of differing sizes, as may be appropriate for different prescriptions.

The arrangement of pucks in a pallet may be determined by the order processing device 114 based on prescriptions that the order processing device 114 decides to launch. The arrangement logic may be implemented directly in the pallet sizing and pucking device 206. Once a prescription is set to be launched, a puck suitable for the appropriate size of container for that prescription may be positioned in a pallet by a robotic arm or pickers. The pallet sizing and pucking device 206 may launch a pallet once pucks have been configured in the pallet.

The loading device 208 may load prescription containers into the pucks on a pallet by a robotic arm, a pick and place mechanism (also referred to as pickers), etc. In various implementations, the loading device 208 has robotic arms or pickers to grasp a prescription container and move it to and from a pallet or a puck. The loading device 208 may also print a label that is appropriate for a container that is to be loaded onto the pallet, and apply the label to the container. The pallet may be located on a conveyor assembly during these operations (e.g., at the high-volume fulfillment center, etc.).

The inspect device 210 may verify that containers in a pallet are correctly labeled and in the correct spot on the pallet. The inspect device 210 may scan the label on one or more containers on the pallet. Labels of containers may be scanned or imaged in full or in part by the inspect device 210. Such imaging may occur after the container has been lifted out of its puck by a robotic arm, picker, etc., or may be otherwise scanned or imaged while retained in the puck. In some implementations, images and/or video captured by the inspect device 210 may be stored in the storage device 110 as order data 118.

The unit of use device 212 may temporarily store, monitor, label, and/or dispense unit of use products. In general, unit of use products are prescription drug products that may be delivered to a user or member without being repackaged at the pharmacy. These products may include pills in a container, pills in a blister pack, inhalers, etc. Prescription drug products dispensed by the unit of use device 212 may be packaged individually or collectively for shipping, or may be shipped in combination with other prescription drugs dispensed by other devices in the high-volume fulfillment center.

At least some of the operations of the devices 206-232 may be directed by the order processing device 114. For example, the manual fulfillment device 216, the review device 218, the automated dispensing device 214, and/or the packing device 226, etc. may receive instructions provided by the order processing device 114.

The automated dispensing device 214 may include one or more devices that dispense prescription drugs or pharmaceuticals into prescription containers in accordance with one or multiple prescription orders. In general, the automated dispensing device 214 may include mechanical and electronic components with, in some implementations, software and/or logic to facilitate pharmaceutical dispensing that would otherwise be performed in a manual fashion by a pharmacist and/or pharmacist technician. For example, the automated dispensing device 214 may include high-volume fillers that fill a number of prescription drug types at a rapid rate and blister pack machines that dispense and pack drugs into a blister pack. Prescription drugs dispensed by the automated dispensing devices 214 may be packaged individually or collectively for shipping, or may be shipped in combination with other prescription drugs dispensed by other devices in the high-volume fulfillment center.

The manual fulfillment device 216 controls how prescriptions are manually fulfilled. For example, the manual fulfillment device 216 may receive or obtain a container and enable fulfillment of the container by a pharmacist or pharmacy technician. In some implementations, the manual fulfillment device 216 provides the filled container to another device in the pharmacy fulfillment devices 112 to be joined with other containers in a prescription order for a user or member.

In general, manual fulfillment may include operations at least partially performed by a pharmacist or a pharmacy technician. For example, a person may retrieve a supply of the prescribed drug, may make an observation, may count out a prescribed quantity of drugs and place them into a prescription container, etc. Some portions of the manual fulfillment process may be automated by use of a machine. For example, counting of capsules, tablets, or pills may be at least partially automated (such as through use of a pill counter). Prescription drugs dispensed by the manual fulfillment device 216 may be packaged individually or collectively for shipping, or may be shipped in combination with other prescription drugs dispensed by other devices in the high-volume fulfillment center.

The review device 218 may process prescription containers to be reviewed by a pharmacist for proper pill count, exception handling, prescription verification, etc. Fulfilled prescriptions may be manually reviewed and/or verified by a pharmacist, as may be required by state or local law. A pharmacist or other licensed pharmacy person who may dispense certain drugs in compliance with local and/or other laws may operate the review device 218 and visually inspect a prescription container that has been filled with a prescription drug. The pharmacist may review, verify, and/or evaluate drug quantity, drug strength, and/or drug interaction concerns, or otherwise perform pharmacist services. The pharmacist may also handle containers which have been flagged as an exception, such as containers with unreadable labels, containers for which the associated prescription order has been canceled, containers with defects, etc. In an example, the manual review can be performed at a manual review station.

The imaging device 220 may image containers once they have been filled with pharmaceuticals. The imaging device 220 may measure a fill height of the pharmaceuticals in the container based on the obtained image to determine if the container is filled to the correct height given the type of pharmaceutical and the number of pills in the prescription. Images of the pills in the container may also be obtained to detect the size of the pills themselves and markings thereon. The images may be transmitted to the order processing device 114 and/or stored in the storage device 110 as part of the order data 118.

The cap device 222 may be used to cap or otherwise seal a prescription container. In some implementations, the cap device 222 may secure a prescription container with a type of cap in accordance with a user preference (e.g., a preference regarding child resistance, etc.), a plan sponsor preference, a prescriber preference, etc. The cap device 222 may also etch a message into the cap, although this process may be performed by a subsequent device in the high-volume fulfillment center.

The accumulation device 224 accumulates various containers of prescription drugs in a prescription order. The accumulation device 224 may accumulate prescription containers from various devices or areas of the pharmacy. For example, the accumulation device 224 may accumulate prescription containers from the unit of use device 212, the automated dispensing device 214, the manual fulfillment device 216, and the review device 218. The accumulation device 224 may be used to group the prescription containers prior to shipment to the member.

The literature device 228 prints, or otherwise generates, literature to include with each prescription drug order. The literature may be printed on multiple sheets of substrates, such as paper, coated paper, printable polymers, or combinations of the above substrates. The literature printed by the literature device 228 may include information required to accompany the prescription drugs included in a prescription order, other information related to prescription drugs in the order, financial information associated with the order (for example, an invoice or an account statement), etc.

In some implementations, the literature device 228 folds or otherwise prepares the literature for inclusion with a prescription drug order (e.g., in a shipping container). In other implementations, the literature device 228 prints the literature and is separate from another device that prepares the printed literature for inclusion with a prescription order.

The packing device 226 packages the prescription order in preparation for shipping the order. The packing device 226 may box, bag, or otherwise package the fulfilled prescription order for delivery. The packing device 226 may further place inserts (e.g., literature or other papers, etc.) into the packaging received from the literature device 228. For example, bulk prescription orders may be shipped in a box, while other prescription orders may be shipped in a bag, which may be a wrap seal bag.

The packing device 226 may label the box or bag with an address and a recipient's name. The label may be printed and affixed to the bag or box, be printed directly onto the bag or box, or otherwise associated with the bag or box. The packing device 226 may sort the box or bag for mailing in an efficient manner (e.g., sort by delivery address, etc.). The packing device 226 may include ice or temperature sensitive elements for prescriptions that are to be kept within a temperature range during shipping (for example, this may be necessary in order to retain efficacy). The ultimate package may then be shipped through postal mail, through a mail order delivery service that ships via ground and/or air (e.g., UPS, FEDEX, or DHL, etc.), through a delivery service, through a locker box at a shipping site (e.g., AMAZON locker or a PO Box, etc.), or otherwise.

The unit of use packing device 230 packages a unit of use prescription order in preparation for shipping the order. The unit of use packing device 230 may include manual scanning of containers to be bagged for shipping to verify each container in the order. In an example implementation, the manual scanning may be performed at a manual scanning station. The pharmacy fulfillment device 112 may also include a mail manifest device 232 to print mailing labels used by the packing device 226 and may print shipping manifests and packing lists.

While the pharmacy fulfillment device 112 in FIG. 2 is shown to include single devices 206-232, multiple devices may be used. When multiple devices are present, the multiple devices may be of the same device type or models, or may be a different device type or model. The types of devices 206-232 shown in FIG. 2 are example devices. In other configurations of the system 100, lesser, additional, or different types of devices may be included.

Moreover, multiple devices may share processing and/or memory resources. The devices 206-232 may be located in the same area or in different locations. For example, the devices 206-232 may be located in a building or set of adjoining buildings. The devices 206-232 may be interconnected (such as by conveyors), networked, and/or otherwise in contact with one another or integrated with one another (e.g., at the high-volume fulfillment center, etc.). In addition, the functionality of a device may be split among a number of discrete devices and/or combined with other devices.

Figure 3:
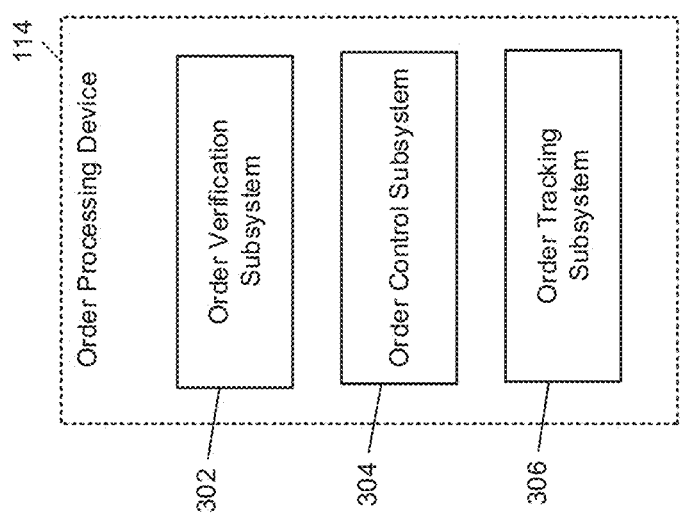
FIG. 3 is a functional block diagram of an example order processing device, which may be deployed within the system of FIG. 1.

FIG. 3 illustrates the order processing device 114 according to an example implementation. The order processing device 114 may be used by one or more operators to generate prescription orders, make routing decisions, make prescription order consolidation decisions, track literature with the system 100, and/or view order status and other order related information. For example, the prescription order may be comprised of order components.

The order processing device 114 may receive instructions to fulfill an order without operator intervention. An order component may include a prescription drug fulfilled by use of a container through the system 100. The order processing device 114 may include an order verification subsystem 302, an order control subsystem 304, and/or an order tracking subsystem 306. Other subsystems may also be included in the order processing device 114.

The order verification subsystem 302 may communicate with the benefit manager device 102 to verify the eligibility of the member and review the formulary to determine appropriate copayment, coinsurance, and deductible for the prescription drug and/or perform a DUR (drug utilization review). Other communications between the order verification subsystem 302 and the benefit manager device 102 may be performed for a variety of purposes.

The order control subsystem 304 controls various movements of the containers and/or pallets along with various filling functions during their progression through the system 100. In some implementations, the order control subsystem 304 may identify the prescribed drug in one or more than one prescription orders as capable of being fulfilled by the automated dispensing device 214. The order control subsystem 304 may determine which prescriptions are to be launched and may determine that a pallet of automated-fill containers is to be launched.

The order control subsystem 304 may determine that an automated-fill prescription of a specific pharmaceutical is to be launched and may examine a queue of orders awaiting fulfillment for other prescription orders, which will be filled with the same pharmaceutical. The order control subsystem 304 may then launch orders with similar automated-fill pharmaceutical needs together in a pallet to the automated dispensing device 214. As the devices 206-232 may be interconnected by a system of conveyors or other container movement systems, the order control subsystem 304 may control various conveyors: for example, to deliver the pallet from the loading device 208 to the manual fulfillment device 216 from the literature device 228, paperwork as needed to fill the prescription.

The order tracking subsystem 306 may track a prescription order during its progress toward fulfillment. The order tracking subsystem 306 may track, record, and/or update order history, order status, etc. The order tracking subsystem 306 may store data locally (for example, in a memory) or as a portion of the order data 118 stored in the storage device 110.

Digital Health Formulary

Digital therapies and interventions include software that prevents, manages, or treats a medical condition. Such digital health solutions may be used by patients independently or in concert with medications or devices (such as a digital scale or blood glucose monitor) to optimize outcomes. Ideally, the digital health solutions are developed according to, and supported by, objective evidence. Further, digital health solutions may be reviewed or cleared by regulatory bodies with respect to claims regarding risk and efficacy and with respect to guidelines for intended use.

Some digital health solutions may require a prescription from a licensed medical practitioner. For some digital health solutions, a prescription may only be required for certain use cases. Other digital health solutions do not require a prescription, but could be ordered or recommended by a licensed medical practitioner. For example only, digital health solutions can be grouped into 3 groups: those used in concert with medication, those used in concert with a device, and those used independently. An example of a digital health solution that is used in concert with a medication includes a sensor that fits onto a controller or rescue inhaler used to treat asthma. The sensor may monitor the frequency of usage of the inhaler and transmit that data back to an app/digital engagement platform where a person can track their usage over time. An example of a digital health solution that is used in concert with a device includes a cellular-enabled blood glucose meter that tracks a person's blood glucose. The meter sends the blood glucose measurements to an app/digital engagement platform where a person can have a visual/graphical representation of their blood glucose over time. An example of a digital health solution that is used independently includes digital cognitive behavioral therapy. Cognitive behavioral therapy is first line psychotherapy (talk therapy) for depression, anxiety and insomnia. Digital cognitive behavioral therapy is a digital (e.g., application based) version of therapy and a person only has to use a computer or mobile device to engage in treatment.

Evaluating claims made by the developers and providers of digital health solutions is a daunting challenge for interested parties, such as health plans, medical professionals, pharmacy benefit managers, and patients. Many of these parties don't have sufficient expertise in the necessary areas-including data science, medicine, UI/UX (user interface and user experience), privacy, information security, and software licensing—much less the available resources to evaluate the range of digital health solutions.

The present disclosure describes an architecture for aggregating information for a wide array of digital health solutions in a digital health marketplace, facilitating management of health plan coverage for digital health solutions via pharmacy benefit managers, and fulfilling prescribed or over-the-counter (OTC) digital health solutions through a virtual pharmacy.

Block Diagram

Figure 4:
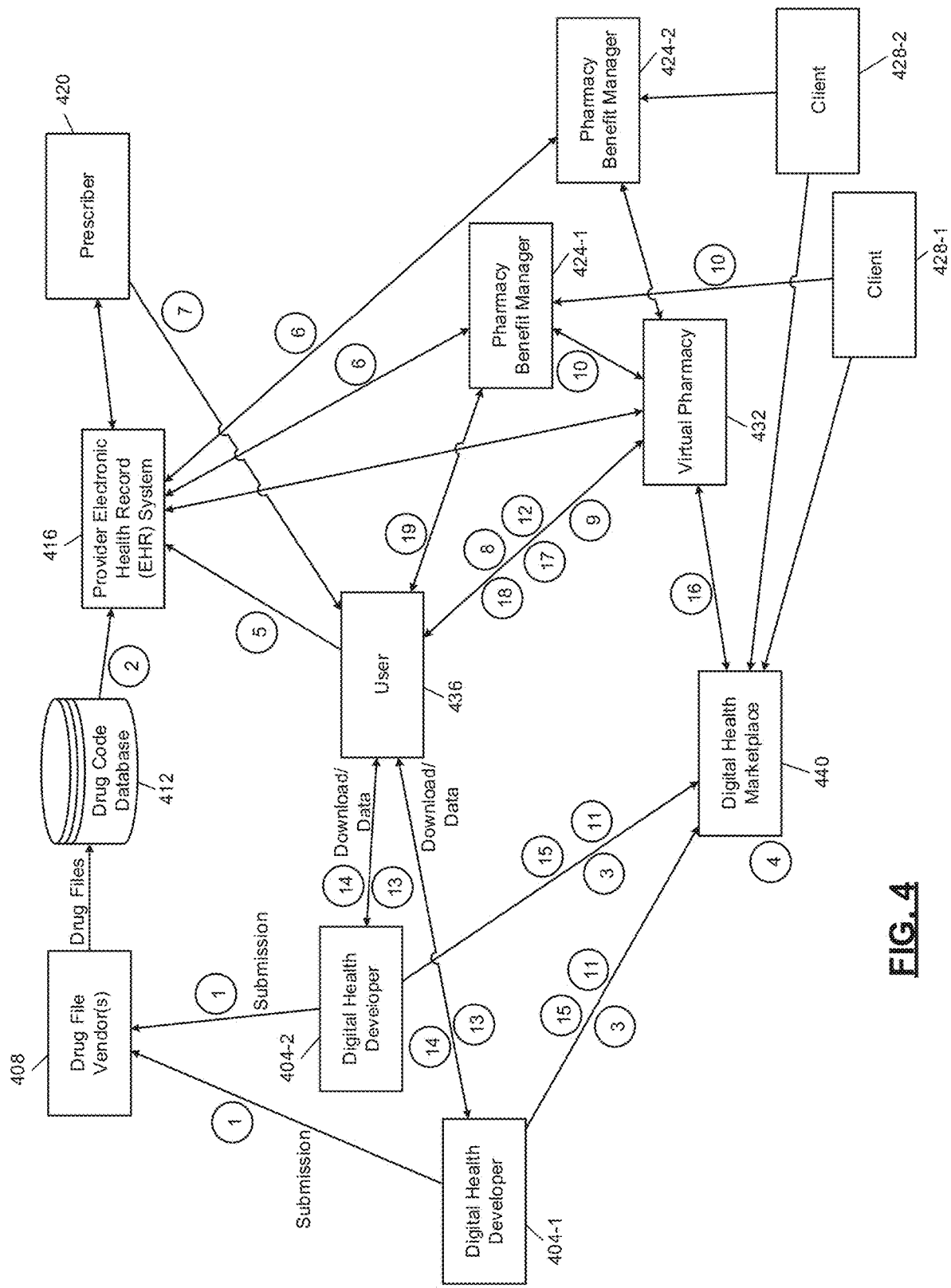
FIG. 4 is a functional block diagram of an example digital health solution distribution architecture.

In FIG. 4, digital health developers 404-1 and 404-2 (collectively, digital health developers 404) have each developed at least one digital health solution. While two are shown for illustration, in practical implementations there will be more digital health developers. The digital health developers 404 submit information about their respective digital health solutions to a drug file vendor 408. While a single rectangle is shown in FIG. 4 for ease of illustration, the digital health developers 404 may submit information to multiple drug file vendors. The drug file vendor 408 may be an existing drug file vendor, such as First Databank (FDB). In various implementations, the digital health developers 404 may submit information to an intermediary for interoperation with existing drug file vendors. In various implementations, one or more new entities may serve the role of a drug file vendor, in some cases in a limited role specific to digital health solutions.

The drug file vendor 408 prepares one or more drug files for a drug code database 412. These drug files may be categorized separately from medications traditionally encoded in drug files. Electronic health record (EHR) systems, such as a provider EHR system 416, rely on the drug code database 412 for populating and displaying data, such as to a prescriber 420. The prescriber 420 may be any medical professional licensed or authored to generate some form of prescription. For example, the prescriber 420 may be a doctor, a physician assistant, a nurse practitioner, etc.

The provider EHR system 416 interacts with one or more pharmacy benefit managers. In FIG. 4, two pharmacy benefit managers are shown for illustration: pharmacy benefit managers 424-1 and 424-2 (collectively, pharmacy benefit managers 424), one or both of which may be implemented by the benefit manager device 102 of FIG. 1. The pharmacy benefit managers 424 allow the provider EHR system 416 to determine coverage and payment information related to digital health solutions. A representative client 428-1 of the pharmacy benefit manager 424-1 is shown for illustration. Similarly, a representative client 428-2 of the pharmacy benefit manager 424-2 is shown for illustration. The clients 428-1 and 428-2 (collectively, clients 428) may be health insurers. The clients 428 supply coverage information to the pharmacy benefit managers 424 so that the pharmacy benefit managers 424 can make coverage and payment determinations.

A virtual pharmacy 432 allows a representative user (device) 436 to browse available digital health solutions, including any prescribed by the prescriber 420. For example only, the virtual pharmacy 432 may be implemented by the pharmacy device 106 of FIG. 1 and include one or more processors. The digital health solutions are aggregated, analyzed, and vetted by a digital health marketplace 440, which receives information about digital health solutions from the digital health developers 404. The digital health marketplace 440 may be embodied by, for example, one or more processors or one or more servers, and serve the virtual pharmacy 432 to users, such as the user 436.

Data Flow

In FIG. 4, circled numbers are displayed at locations (such as arrows indicating data interchange) where additional information will be described. The numbers do not necessarily imply an order. At location 1, the digital health developers 404 submit information for digital health solutions to the drug file vendor 408 for inclusion in the drug code database 412.

At location 2, the drug code database 412 sends information—for example, an NDC (national drug code) (e.g., associated with a digital health solution)—to the provider EHR system 416 for use by health care providers, including the representative prescriber 420. In various implementations, the drug file vendor 408 may not have defined NDCs for digital health solutions and so the digital health marketplace 440 may define proprietary NDCs for the (digital health) solutions from the digital health developers 404.

At location 3, the digital health developers 404 submit their digital health solutions to the digital health marketplace 440 for evaluation. The digital health developers 404 may also transmit other information to the digital health marketplace 440.

At location 4, professionals at or associated with the digital health marketplace 440 evaluate and score the digital health solutions based on criteria such as usability, technical scalability, security, adoption, empirical result data, etc. In various implementations, the digital health marketplace 440 may be configured to evaluate and score the digital health solutions automatically, for example, using machine learning. This information may allow the clients 428 to make informed decisions regarding inclusion of the digital health solutions in a digital health formulary. This information may also permit the virtual pharmacy 432 to prepare a tiered ranking of digital health solutions. For example, the digital health marketplace 440 may allow members to log in and see digital health solutions that the members are eligible for based on meeting predetermined clinical criteria and what the members' health benefits plans have paid for. In various implementations, the virtual pharmacy 432 may be configured to determine the tiered rankings automatically, for example, using machine learning. The digital health solutions that were successfully vetted may be combined into a digital health formulary maintained by the digital health marketplace 440. Carton tiers for each criterion may indicate successful vetting.

The vetting may be performed, for example, by expert panels employed by or coordinated by the digital health marketplace 440 and/or PBMs 424. The expert panels may include doctors, health policy PhD and Pharm.D. degree holders, certified digital usability and accessibility experts, etc. The experts may assess clinical and usability components of the digital health solutions. In addition, a value assessment may be performed on the digital health solutions, which may attempt to determine a return-on-investment based on established efficacy and pricing models of the digital health solutions. In addition, the digital health marketplace 440 may negotiate pricing models with the digital health developers 404, which may include per-person per-month costs with tiered volume discounts. Alternatively, evaluators of the digital health solutions may negotiate pricing models with the digital health developers 404. In various implementations, the digital health marketplace 440 may be configured to perform the vetting automatically, for example, using machine learning.

At location 5, the user 436 visits a medical provider (e.g., prescriber 420) that uses the provider EHR system 416.

At location 6, the medical provider (e.g., prescriber 420) checks for digital health solution formulary and eligibility of the user 436 based on health plan coverage. Depending on the identity of the user 436, the provider EHR system 416 may contact either the pharmacy benefit manager 424-1 or the pharmacy benefit manager 424-2 to perform these checks. In various implementations, the provider EHR system 416 may perform the formulary and eligibility checks for the user 436 in advance of the visit. For example, the provider EHR system 416 may batch process checks overnight for all scheduled visits the following day. In this way, the prescriber 420 can have instant access to eligibility and, in some cases, cost information.

In addition, the pharmacy benefit managers 424 may provide recommendations of digital health solutions relevant to the users to the provider EHR system 416 using, for example, an interface developed based on Fast Healthcare Interoperability Resources (FHIR). In various implementations, the pharmacy benefit managers 424 may determine the recommendations automatically, such as using machine learning. These recommendations could be presented to the prescriber 420 using, for example, a clinical guidance message in the provider EHR system 416. Other capabilities to present opportunities to the prescriber 420 as part of their workflows include HL7 FHIR application programming interfaces (APIs), Substitutable Medical Applications, Reusable Technologies (SMART) on FHIR apps, National Council for Prescription Drug Programs (NCPDP) standard electronic prescribing formats, and Clinical Direct messaging. The digital health market place digital channels and adjudication system may directly interact with the APIs to update data and perform transactions.

In conjunction with, or independent of, a scheduled visit, the pharmacy benefit managers 424 may provide recommendations of relevant prescription digital health solutions directly to the user 436. If interested, the user 436 can directly convey their interest in a prescription digital health solution to the prescriber 420, such as during an in-person visit. Additionally or alternatively, if the user 436 indicates interest in the prescription digital health solution using the virtual pharmacy 432, a prescription request could be provided to the prescriber 420, such as via the provider EHR system 416.

At location 7, the prescriber 420 provides a prescription for a digital health solution to the user 436. The prescription may be paper-based. In various implementations, the prescriber 420 may additionally or alternatively generate an electronic prescription for the user 436. The (electronic) prescription may be entered into the provider EHR system 416, which may communicate the electronic prescription to the virtual pharmacy 432.

At location 8, if the user 436 has already registered with the virtual pharmacy 432, the virtual pharmacy 432 may transmit a notification to the user 436 in response to receiving the prescription. For example, this notification may take the form of one or more of a text (or SMS) message, an email, a smartphone notification, an automated or personal voice call, etc. To access the virtual pharmacy 432, the user 436 may navigate, using a web browser on a smartphone or computer, to a web portal operated by the virtual pharmacy 432. The user 436 may additionally or alternatively access the virtual pharmacy 432 via executing a downloaded mobile application that interfaces with the virtual pharmacy 432. The mobile application may be obtained from a digital distribution platform, such as the GOOGLE PLAY digital distribution platform from Google LLC or the APP STORE digital distribution platform from Apple Inc. Example user interfaces for the mobile application are described below.

If the user 436 received a paper prescription, the paper prescription may include a uniform resource locator (URL)—for example a relatively short URL that can be easily typed—and/or a quick response (QR) code that can be scanned by a smartphone and decoded to reach a corresponding URL. The URL may connect the user 436 to a web portal of the virtual pharmacy 432. Additionally or alternatively, the website at the URL may include instructions regarding downloading a mobile application, including links to popular digital distribution platforms.

At location 9, the user 436 accesses the virtual pharmacy 432 to review digital health solutions, including those that have been prescribed as well as potentially others that may be available. In various implementations, the digital health marketplace 440 may display digital health solutions that are found in the same category within the digital health formulary as the prescribed digital health solution. This may be similar to the way that generics are available (or mandated) as alternatives to brand-name medications.

The virtual pharmacy 432 may allow for reviews to be submitted by the community. These reviews may be subject to moderation before or after being posted. The virtual pharmacy 432 may also display usage data collected via the digital health marketplace 440. For example, the usage data may include an average number of monthly users, a total number of lifetime users, monthly retention percentages, etc.

When the user 436 accesses the virtual pharmacy 432 in an over the counter (OTC) model (for example, if no prescriptions have been submitted for the user 436), the virtual pharmacy 432 may ask the user 436 a set of questions. Based on symptoms and needs revealed by answers to this set of questions, the virtual pharmacy 432 can recommend one or more digital health solutions to the user 436. The set of questions may be generated by a decision tree and/or a decision table implemented by a rules engine.

The virtual pharmacy 432 may implement a recommendation engine that takes the answers as inputs and generates a set of recommended digital health solution options for provision to the user 436. The recommendations may indicate whether a particular digital health solution is covered by their plan or not, along with pricing.

With or without recommendations, the user 436 may search through the digital health solutions in the virtual pharmacy 432 by category, symptoms, disease state, etc. The user 436 may be able to filter based on various criteria, including coverage and pricing.

As indicated at location 10, the coverage may be determined in real-time from an adjudication interface of one of the pharmacy benefit managers 424. For example, the adjudication interface of the DHSs may be developed based on FHIR. Additionally or alternatively, pricing may be determined in real-time from the adjudication interface of one of the pharmacy benefit managers 424.

The recommendations may be ranked according to coverage, pricing, and information provided by the digital health marketplace 440. For example, this information may include recommendation tiers (with higher tiers being reserved for digital health solutions that expert panels have determined to be efficacious, user-friendly, and offering a higher return on investment). The information may also include user feedback, social media impressions, adoption rate, etc.

At location 11, the digital health marketplace 440 determines activation criteria for the digital health solutions offered by the digital health developers 404. The activation criteria may include an activation token or activation code. For other digital health solutions, the activation criteria may be tied to unique identifying data. For example, the digital health developer 404-1 may permit access to a user who can demonstrate possession of a particular phone number or email address. In such a case, fulfilling (also referred to as "filling" or "dispensing") an order for the digital health solution on behalf of the user 436 may include the virtual pharmacy 432 providing the email address or phone number of the user 436 to the digital health marketplace 440. The DHM then passes the contact information to the digital health developer 404-1.

In another case, the digital health developer 404-2 may generate an activation token or activation code for each user. The digital health marketplace 440 may obtain an activation token/code in order to fulfill an order by the user 436. For some (or all) of the digital health solutions, the digital health marketplace 440 may instead cache one or more activation tokens/codes that can be immediately provided to the user 436 without requiring any additional communication with the digital health developers 404. Even when communication is not necessary, the respective one of the digital health marketplace 440 may advise the digital health developers 404 when an activation token/code has been assigned.

At location 12, the virtual pharmacy 432 provides the user 436 with a mechanism to access the digital health solution. This access mechanism may include an activation token/code. For example, the activation token/code may be embedded in a URL used to access or download the digital health solution. In other cases, as indicated above, possession of a particular phone number or email address (which may be verified by sending a randomized code via text or email, respectively) or activation code may be sufficient for activation.

The access mechanism may be a link to a digital distribution platform corresponding to an operating system on the device operated by the user 436. By using all-digital channels, the entire fulfillment workflow from prescription to obtaining the digital health solution may be accomplished within minutes. For example, adjudication may be performed by one of the pharmacy benefit managers 424 while a notification is supplied to the user 436 of availability of the digital health solution. In various implementations, that notification can be recalled in the event of unsuccessful adjudication. The user 436 may review terms of service for the digital health solution and then proceed to obtaining the digital health solution with a single click/tap following submission of a prescription by the prescriber 420.

At location 13, the user 436 downloads and activates the digital health solution. If the download is to a mobile device, the download may occur from a digital distribution platform to which the digital health developers 404 have uploaded their mobile apps, rather than from the digital health developers 404 themselves.

At location 14, the digital health developers 404 may collect usage data, which may be used to assess efficacy and comply with regulations. The usage data may include frequency of usage, length of use, etc.

At location 15, the data collected by the digital health developers 404 is shared with the digital health marketplace 440 in near real-time or on a schedule, such as nightly. If one or more predetermined patterns emerge (e.g., repeated elevated blood glucose measurements), this data can be used to trigger an outreach, such as by a pharmacist, to counsel the member, such as discussed further below. The data may be housed in various places and not necessary in the digital health marketplace 440.

At location 16, the digital health marketplace 440 updates rankings of digital health solutions based on usage data. For example, these changes may be made in near-real-time as new usage data is received. These changes may be reflected immediately in results shown by the virtual pharmacy 432.

The digital health marketplace 440 may also be able to, in real time, "recall" the digital health solution from the virtual pharmacy 432 (akin to taking a medication off the shelf in a physical pharmacy). Such a recall may be performed if a security or other issue is identified.

The digital health marketplace 440 and the virtual pharmacy 432 may have a two-way data synchronization, where the digital health marketplace 440 provides aggregated usage data per product (anonymized) and the virtual pharmacy 432 provides aggregated usage data per customer (also anonymized) as well as any community-driven data (e.g. reviews, feedback, etc.).

The digital health marketplace 440 may use the combined data set, as well as analysis of public news and social media through data mining and natural language processing (NLP) technology to provide an analytical view of a preferred ranking recommendation in near-real-time. The digital health marketplace 440 may also leverage the same data analysis technology above to understand any potential product risk, especially those involving non-medical situations (system crash, data leak, etc.). A human representative at the digital health marketplace 440 may be alerted in response to a determination that a digital health solution may need to be temporarily rendered unavailable.

At location 17, the virtual pharmacy 432 may provide real-time notification to the user 436 via their preferred channel on any app or usage updates, recalls, formulary changes, refills, etc.

At location 18, the user 436 may perform a refill through the virtual pharmacy 432, either automatically or with a minimal number of clicks/taps. With a digital health solution already installed on a mobile phone, the user 436 can indicate their desire to refill automatically (which may require reaching agreement on an upper price threshold). In various implementations, the upper price threshold may be set to free so that automatic refills occur so long as the digital health solution is still covered with no co-pay by the health plan. In the context of digital health solutions, a refill may simply be continuing to use the digital health solution, such as for another month or year. When enabled, the refill request and confirmation could be handled completely behind the scenes between the virtual pharmacy 432 and the digital health developers 404.

At location 19, the pharmacy benefit manager 424-1 (assuming that the pharmacy benefit manager 424-1 is the relevant PBM for the user 436) can use real-time and historical claims information to recommend OTC digital health solutions to the user 436 that are in the formulary on their corresponding health plan. For example, the pharmacy benefit manager 424-1 may be programmed to identify symptoms based on claims history for the user 436. Meanwhile, the pharmacy benefit manager 424-1 synchronizes with the digital health marketplace 440 to create a clinical mapping between symptoms and relevant digital health solutions.

As new or better digital health solutions relevant to the user 436 are identified by the pharmacy benefit manager 424-1, a notification can be provided to the user 436. In fact, the notification can be sent to the user 436 even if the user 436 has not yet registered to use the virtual pharmacy 432 or has even heard of the virtual pharmacy 432. In various implementations, other entities may perform similar recommendation functions. However, these entities may need to obtain access to claims data from the pharmacy benefit manager 424-1 or medical data from another source, such as the provider EHR system 416.

User Interface

Figure 5:
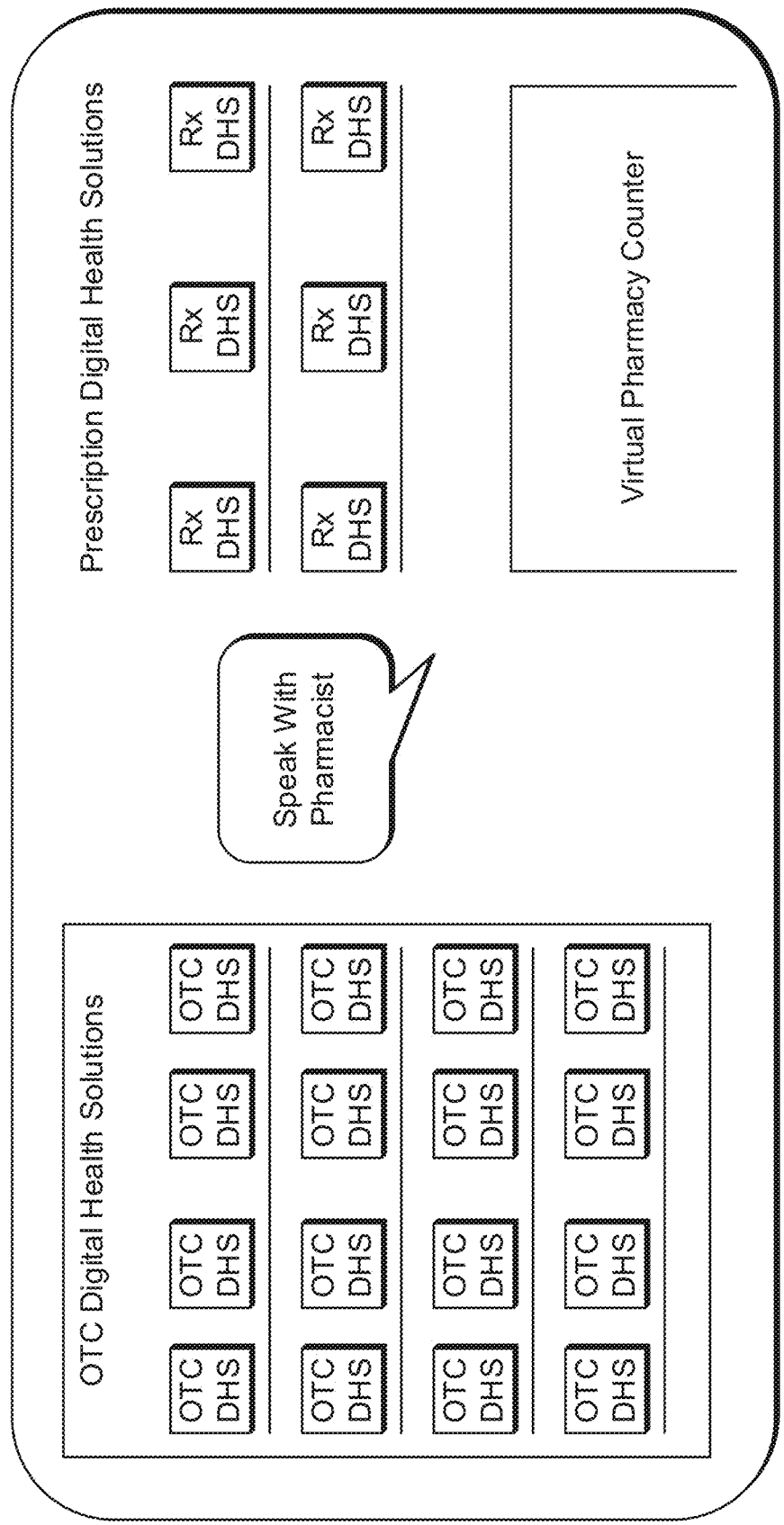
FIG. 5 is a graphical representation of an example web-based interface for the virtual pharmacy.

FIG. 5 is an example web-based interface for the virtual pharmacy 432. The interface includes virtual "shelves" of OTC digital health solutions (abbreviated as DHS), a virtual pharmacy counter with prescription digital health solutions "behind the counter," and a button for the user to request a conversation with a pharmacist chatbot triage. Digital therapeutics (sometimes abbreviated DTx) are a type of digital health solution.

In various implementations, the user is only shown the OTC digital health solutions that are specifically clinically targeted for the user and are covered by their health plan (e.g., as determined by a pharmacy benefit manager).

Although covered, the cost may still be non-zero. In other implementations, the user may be presented with all of the OTC digital health solutions by category (e.g., pulmonary, cardiovascular) or by symptom (e.g., depression). Each OTC digital health solution may be displayed with an indication (such as an icon) of whether the OTC digital health solution is covered or not.

If the user selects an OTC digital health solution that is covered, the user may be taken through a clinical eligibility screening via the OTC digital health solution developer. If the user is clinically eligible for the OTC digital health solution, then the user is allowed to enroll and either pays in full personally, pays a copay, or pays nothing, depending on plan coverage. As described above, in response to payment, the user may receive a download link to the digital health solution. The download link may include an embedded activation code. The user may download the digital health solution to a computing device for execution via the download link and/or the activation code.

If the user selects an OTC digital health solution that is not covered by their benefit plan, the user may still be taken through a clinical eligibility screening via the OTC digital health solution developer. If the user is clinically eligible for the OTC digital health solution, then the user is allowed to enroll and pays full price for the OTC digital health solution. The full price may have been negotiated by the digital health marketplace 440.

If the user was prescribed a prescription digital health solution, then an adjudication and drug utilization review (DUR) may have been performed at the time of submission of the prescription digital health solution. Assuming successful adjudication and DUR, the user may see the prescription digital health solution waiting for them "behind the counter" of the virtual pharmacy. Examples of behind the counter prescription digital health solutions are illustrated in FIG. 5 by Rx DHS. The user can then enroll and, depending on plan coverage, either pay nothing, the appropriate co-pay, or in full.

In FIGS. 6A-6E, example smartphone user interfaces for a digital health hub (e.g., digital health marketplace) are shown. The smartphone user interfaces may be displayed to a user via a display of a smartphone, a tablet, or another suitable type of computing device.

Figure 6C:
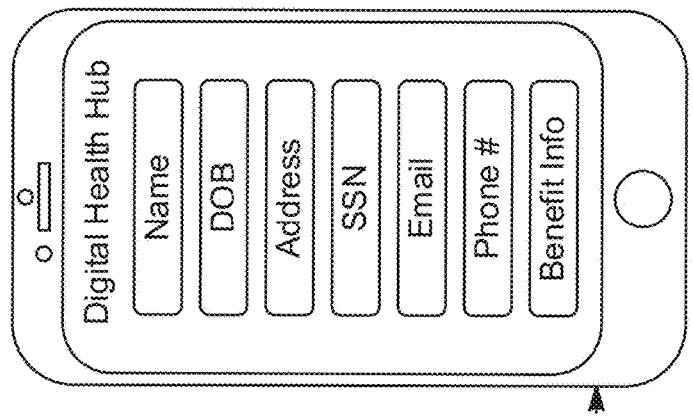
Figure 6B:
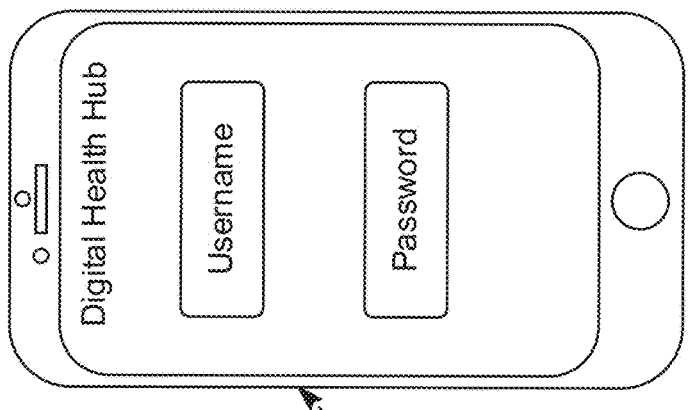
Figure 6A:
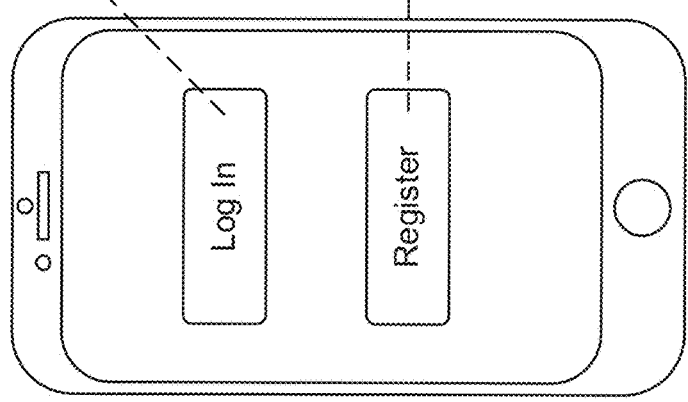

In FIG. 6A, the user can select whether to register for the first time (leading to a registration process depicted in FIG. 6C) or log in (leading to a login process depicted in FIG. 6B). In FIG. 6B, the user supplies a username and password and, if multi-factor authentication is enabled, presents another factor. In FIG. 6C, the user supplies personally-identifiable information. If the user is known to the virtual pharmacy, such as if the virtual pharmacy shares personally-identifiable information with a pharmacy benefit manager (as may be the case where they are operated by a common entity), then benefit information may automatically be pulled into the virtual pharmacy from the pharmacy benefit manager. Otherwise, the user may have to enter/input benefit information, such as health plan enrollee or group identifiers, or the personally identifiable information, such as name, date of birth (DOB), address, social security number (SSN), and email.

FIG. 6D depicts an example welcome screen presented to the user upon successful login via inputting a username and a password of a previously registered account. Selecting the button for "Your Medicine Cabinet" causes the application to transition to an interface such as that depicted in FIG. 6E. The selection may be, for example, a touch input received within boundaries of the button.

In FIG. 6E, the user is presented with their OTC and prescription digital health solutions. The user may also be presented with their medication history via a medical-history application programming interface (API). Additionally, a "health summary" section may be displayed with data, such as average blood glucose, average blood pressure, and/or weight over a historical period, such as the prior week or month. Information in the health summary can be displayed pictorially, graphically, or numerically.

The user may be able to directly access each digital health solution through the app by pressing the corresponding button (e.g., OTC DHS 1, OTC DHS, 2, Rx DHS 1). Authentication to the digital health solutions may be handled via a single-sign-on mechanism so that the user does not have to maintain separate credentials for each of the digital health solutions.

The application may accumulate data, such as usage data and medical data, from each of the digital health solutions and feed the accumulated information back to the virtual pharmacy via a real-time API. This may eliminate the need for batch data transfers from or to the digital health solution developers.

Data may also be transferred from the virtual pharmacy or the digital health solution developers to a Health Action Plan (HAP) portal. The HAP portal allows Therapeutic Resource Center (TRC) pharmacists—pharmacists that are disease specialized, answer medication questions from users, and monitor clinical alerts—to view clinical alerts and reach out to users.

Figures 7D, 7E:
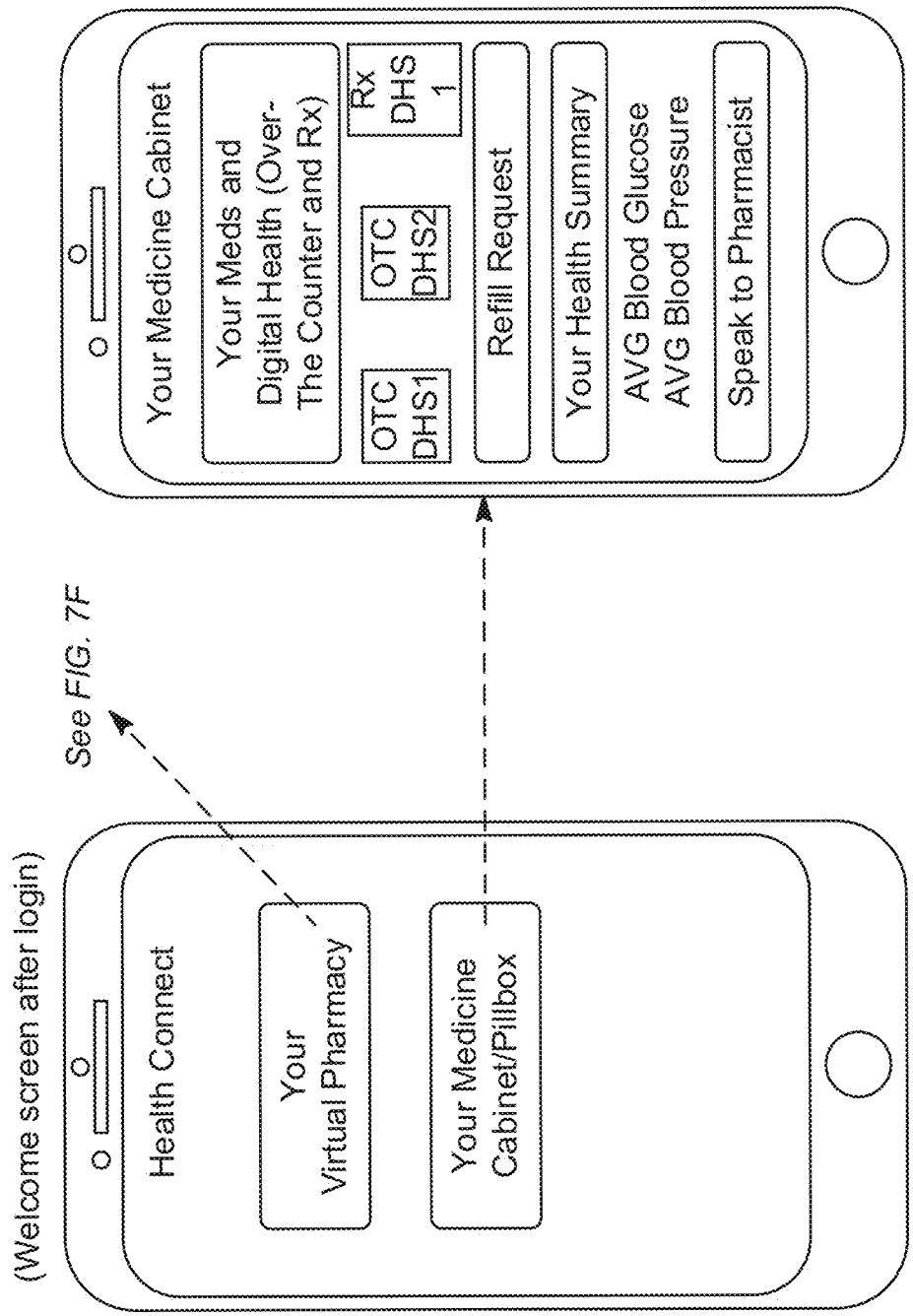

FIGS. 7A-7H are example smartphone user interfaces for a health connect application that may be displayed. The smartphone user interfaces may be displayed to a user via a display of a smartphone, a tablet, or another suitable type of computing device. FIG. 7A represents an initial screen presented to the user upon launching of the health connect application. In response to selection of the login option, the user interface of FIG. 7B may be presented. FIG. 7B may allow a user to login by inputting a username and a password associated with a previously registered account. In response to selection of the register option, the user interface of FIG. 7C may be presented. FIG. 7C may allow a user to create and register a new account.

Upon successful login or registration, the user interface of FIG. 7D may be presented. In response to the user selecting "Your Virtual Pharmacy," the user interface of FIG. 7F may be presented. In response to the user selecting "Your Medicine Cabinet/Pillbox," FIG. 7E may be presented.

In FIG. 7F, the user is presented with the choice between their prescriptions and shopping for other digital health solutions. In response to the user selecting "Shop," the user interface of FIG. 7G may be presented. In response to the user selecting "Your Rx," FIG. 7H may be presented. Presentation as used herein may include at least one of a display of information on a display and audible output of information via one or more speakers.

The user interface of FIG. 7G may separate OTC digital health solutions that are covered under the user's benefits coverage from OTC digital health solutions that are not covered under the user's benefit coverage. The user interface of FIG. 7G may also include a button for the user to request a conversation with a pharmacist chatbot triage or live phone call for any medication related questions.

The user interface of FIG. 7H may separate digital health solutions prescribed to the user by prescriber. The user interface of FIG. 7H may also include a button for the user to request a conversation with a pharmacist chatbot triage.

Figure 8:
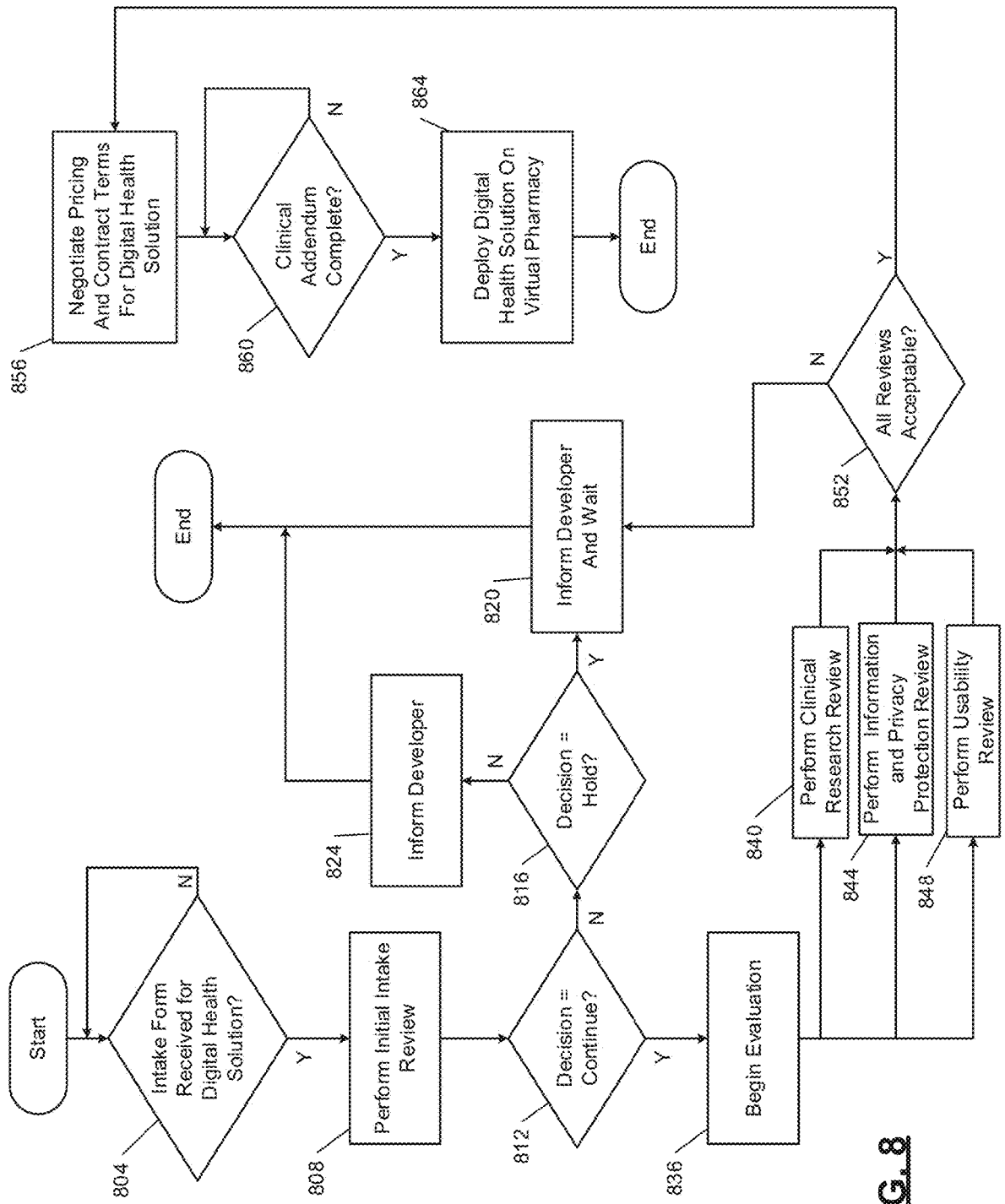
FIG. 8 is a flowchart depicting an example method of deploying a digital health solution on a virtual pharmacy.

FIG. 8 is a flowchart depicting an example method of deploying a digital health solution on the virtual pharmacy 432. Control begins with 804 where the digital health marketplace 440 determines whether an intake form has been received from a digital health developer 404 for a new digital health solution that is proposed to be distributed via the virtual pharmacy 432. If 804 is true, control continues with 808. If 804 is false, control remains at 804 or may end.

At 808, an initial intake review is performed. The initial intake review may be performed via a review of the intake form, for example, by a panel including one or more pharmacists, physicians, health outcomes research professionals having PhDs, a PBM digital product team, and user experience experts with knowledge in usability, accessibility, and member experience. The intake form provides the panel with answers to a set of pertinent questions that guide the determination regarding whether the digital health developer 404 should move on to the next stage of the vetting process. The initial intake review includes: (a) a clinical review, (b) a privacy, security, and stability review, and (c) a business and accountability review. The clinical review includes a review of: (i) credentials of medical personnel on developer's staff, (ii) a review of whether the developer is solving a clinical problem that needs a solution via the digital health solution, (iii) the developer's clinical approach to the solution, (iv) a review of presented clinical evidence, (v) a review of research methodology, (vi) a review of statistical significance of results, and (vii) an effect of the solution if used incorrectly. The privacy, security, and stability review includes reviewing (i) a HITRUST certification or a SOC II mapping to HITRUST certification and (ii) scalability. The business and accessibility review includes reviewing (i) whether the developer has articulated a clinical pain point, problem statement, and proposed solution, (ii) a number of members utilizing the developer's solution, (iii) a length of time that the developer has been in business, and (iv) web content accessibility and guidelines (WCAG) 2.0 compliance of the developer. There may also be a usability review which includes member experience experts that test user-friendliness, tracking and syncing with other devices, and ensure accessibility requirements (e.g., WCAG 2.0) are met.

The initial intake review results in a decision to one of: continue vetting; hold vetting for more information; and reject (at least for now) the opportunity to distribute the digital health solution via the virtual pharmacy 432.

At 812, a determination is made whether the decision (from the initial intake review) is to continue with the vetting of the distributor and the digital health solution. If 812 is true, control continues with 836, which is discussed further below. If 812 is false, control transfers to 816. At 816, a determination is made whether the decision (from the initial intake review) is to hold vetting. If 816 is true, the developer is informed of the decision to wait for more data, public research, or a potential pilot opportunity in the future at 820. If 816 is false, the developer is informed of the decision to deny the opportunity at 824. Feedback and reasoning may be given to the distributor if requested. The feedback may encourage the developer to re-submit an intake form in the future once areas of opportunity and/or weakness are addressed.

At 836 (when the decision from the initial intake review is to continue), evaluation of the developer and the digital health solution is begun. A non-disclosure agreement may also be entered into with the developer. The evaluation includes performing a clinical research review at 840, an information and privacy protection review at 844, and a usability review at 848. 840, 844, and 848 may be performed in parallel, for example, to minimize the period necessary to complete the evaluation, or sequentially, for example, to minimize resources. 840, 844, and 848 may be performed by different groups, for example, for increased accuracy of the results of the evaluation.

The clinical research review may be performed at 840, for example, by a group of health researchers (e.g., PhD level), medical doctors, and others. 840 may include reviewing all public studies, posters, published outcomes, ROI methodology, food and drug association (FDA) dossiers if any, and pre-released documents provided by the developer. The information and privacy protection review may be performed at 844, for example, by digital product and clinical teams. 844 may include a review of usability of the digital health solution. A full, live demo of the digital health solution may be navigated and tested by the digital product and clinical teams. Others may also test the demo, such as individuals living with or directly impacted by the condition mitigated by the digital health solution. The following areas may be examined during 844: (i) flow and logic of the digital health solution, (ii) engagement strategy of the digital health solution, (iii) ease of syncing of any (external) devices to the digital health solution, (iv) ability of the digital health solution to integrate into the flow of a potential users everyday life, and (v) whether any clinical language and recommendations made within the digital health solution satisfy one or more standards. 844 may also include ensuring that the digital health solution is compliant with one or more accessibility guidelines, such as to ensure that the digital health solution could be made available to all users of the virtual pharmacy 432.

Because the developer may be able to access protected health information (PHI) and personally identifiable information (PII) if the digital health solution is deployed, 848 may include reviewing security of the developer to ensure that the developer satisfies one or more security standards. This may include completion and review of a security questionnaire, assessment of security capabilities and maturity of the developer, a vulnerability assessment of the digital health solution, inspection of evidence of compliance with the security standard(s), security alignment to service industry standards, such as HITRUST, NIST, HIPPA, and payment card industry standards. 848 may also include completion of a risk assessment of the developer.

In various implementations, the reviews of 840-848 may be performed automatically, for example, using trained machine learning models or in another suitable automated manner.

At 852, control determines whether the reviews of 840-848 have all indicated that the digital health solution, developer, or both are acceptable. If 852 is false, control may transfer to 820, as discussed above. If 852 is true, control may continue with 856.

At 856, contract terms and pricing for the digital health solution are negotiated with the developer of the digital health solution. At 860, a determination is made regarding whether a clinical addendum has been completed, if necessary. If 860 is true, the digital health marketplace 440 makes the digital health solution available via the virtual pharmacy 432 at 864, and control may end. If 860 is false, control may remain at 860. In various implementations, 860 may be omitted.

In FIG. 9, another example smartphone user interface for a digital health hub (e.g., virtual pharmacy) is shown. As shown in FIG. 9, the virtual pharmacy may also display devices in addition to digital health solutions (applications).

The devices may be connectable to user devices or available for purchase via the virtual pharmacy.

Figure 10:
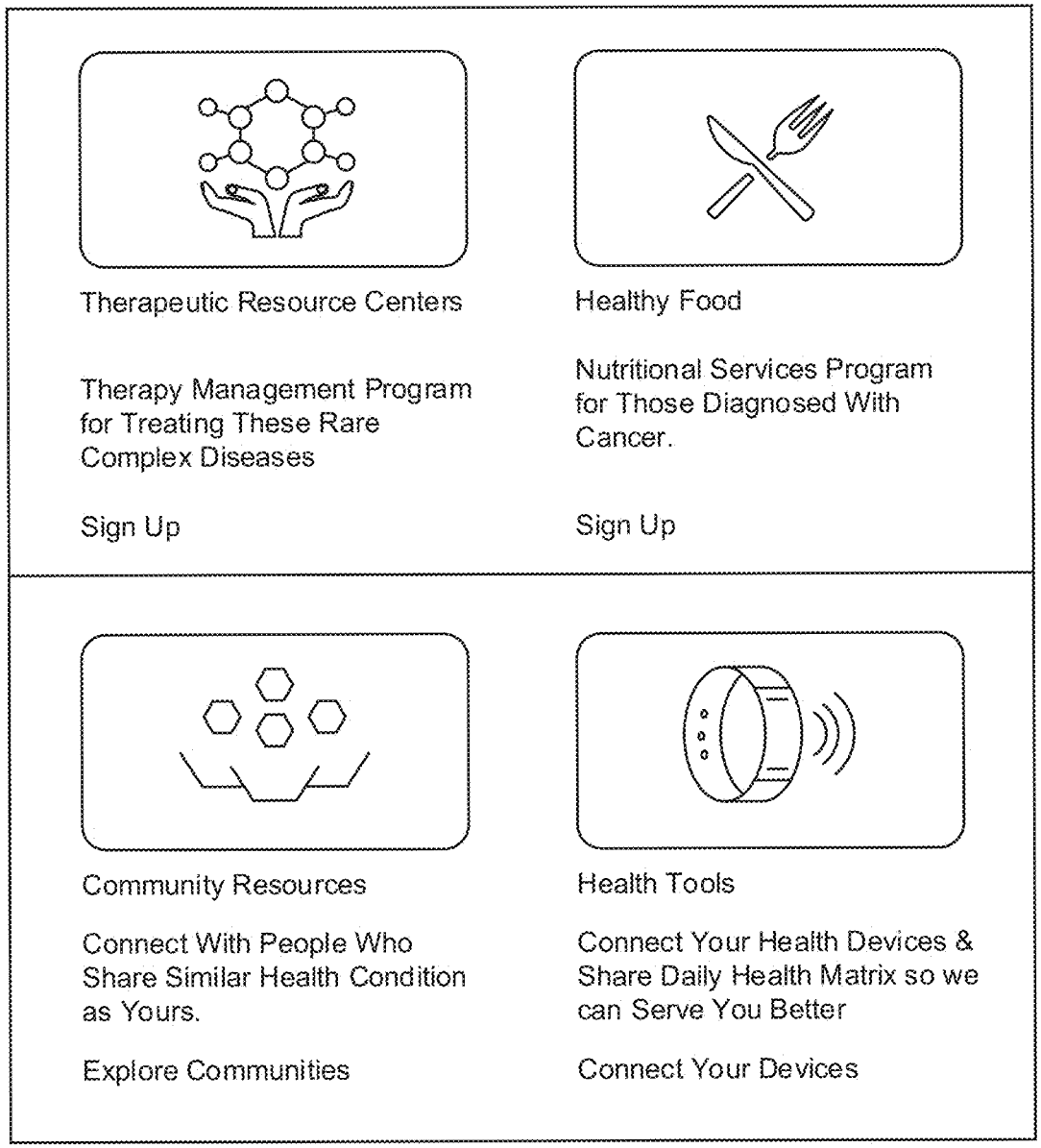

In FIGS. 10 and 11 other example smartphone user interfaces for a digital health hub (e.g., virtual pharmacy) are shown. As shown in FIG. 10, the virtual pharmacy may also display links to resources that are non-disease specific (general). These may be referred to as general wellness resources. As shown in FIG. 11, the virtual pharmacy may also display links to resources that are disease specific (i.e., specific to a disease of the user). Examples include disease specific partner programs, disease specific therapeutic resources, disease specific cuisine (e.g., via a partner, such as Therapease cuisine), disease specific community resources, etc.

Figure 12:
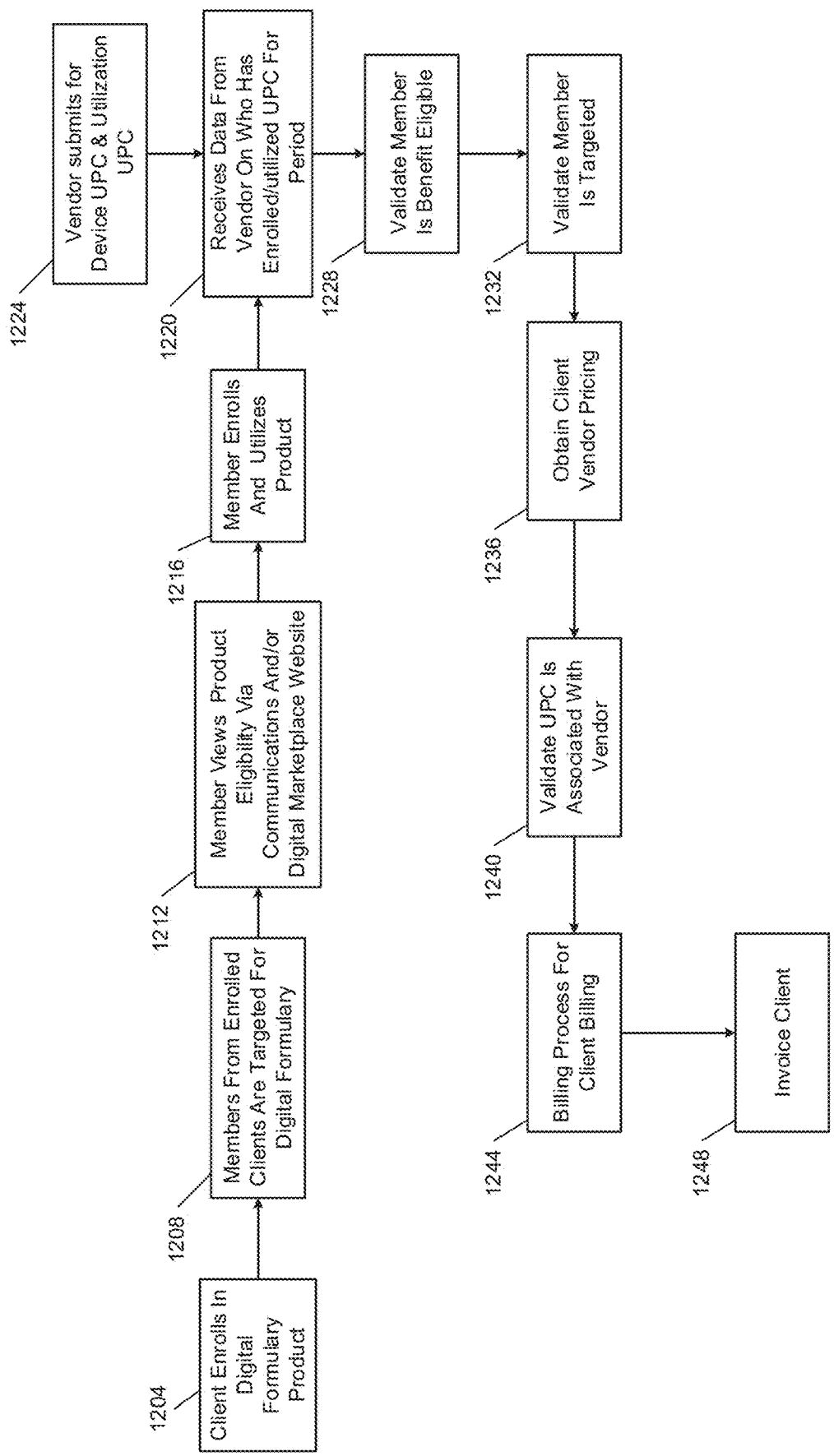

FIG. 12 is a flowchart depicting an example method of digital health solution (product) distribution, control, and billing. Control begins with 1204 where a client (a user) enrolls in use of a digital formulary product. Digital formulary products include digital health solutions (e.g., applications). At 1208, the virtual pharmacy may target one or more users from enrolled clients are targeted by the virtual pharmacy for use of the digital formulary product. The virtual pharmacy may target users, for example, based on the users having symptoms or diseases that are associated with the digital formulary product.

At 1212, the targeted (or non-targeted) members view product eligibility information for the digital formulary product via communications (e.g., letters, emails, messages, etc.) regarding the digital formulary product and/or other information, such as the digital health marketplace and/or a website associated with the digital formulary product. At 1216, a member enrolls for use in the digital formulary product and utilizes the digital formulary product, such as by executing the digital formulary product on a user device.

At 1220, the virtual pharmacy receives data from the vendor of the digital formulary product regarding which one or more members have used the digital formulary product (e.g., the unique product code, UPC, associated with the digital formulary product for at least a predetermined period (e.g., 1 month). At 1224, the vendor of the digital formulary product submits utilization information (e.g., period of use) for each digital formulary product of the vendor and for each unique user device (e.g., a UPC of the user device) using that digital formulary product.

At 1228, the virtual pharmacy determined whether (or verifies that) the member is eligible for a benefit, such as a price reduction for the digital formulary product etc. At 1232, the virtual pharmacy determines whether (or verifies that) the member has been targeted for use of the digital formulary product.

At 1236, the virtual pharmacy obtains pricing for the digital formulary product between clients (including the member) and the vendor of the digital formulary product. At 1240, the virtual pharmacy validates that the UPC of the digital formulary product is associated with (of) the vendor. This ensures that payment for the digital formulary product is routed to the proper vendor. At 1244, a pharmacy benefit manager performs billing associated with billing a client (e.g., an insurance carrier) for the digital formulary product use by the member. At 1248, the pharmacy benefit manager transmits an invoice to the client for the use of the digital formulary product by the member.

Figure 13:
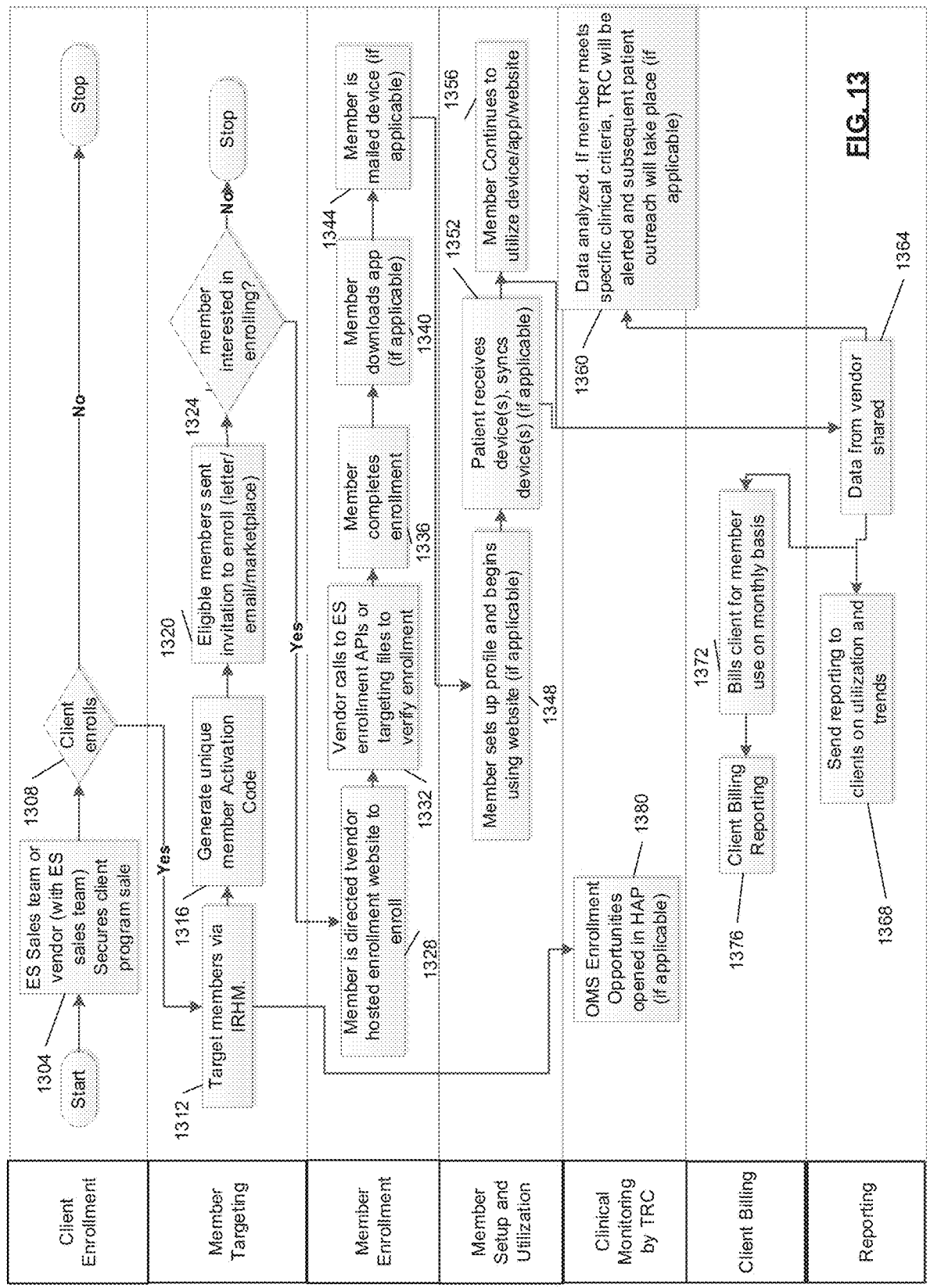

FIG. 13 is flowchart regarding use of a digital formulary product by a member. At 1304, a client program sale is secured, such as by a sales team associated with the virtual pharmacy or vendor along with such a sales team. At 1308, a determination is made regarding whether a client (e.g., an insurance carrier or a member) has enrolled. If 1308 is true, control may continue with 1312. If 1308 is false, control may end.

At 1312, one or more members of the client are targeted using an integrated human resource management (IHRM) system. The IHRM may use machine learning to determine which members to target. Alternatively, one or more individuals may determine which members to target. At 1316, the virtual pharmacy generates activation criteria (e.g., unique member activation codes) for targeted members. At 1320, the virtual pharmacy sends (and the targeted members receive) invitations to enroll in use of the digital pharmacy product and include the unique activation criteria generated for the targeted members. The virtual pharmacy may send, for example, letters, emails, messages, etc. indicative of the offer to enroll for the use of the digital pharmacy product. At 1324, the virtual pharmacy determines whether a targeted member is interested in enrolling for use of the digital pharmacy product. If 1324 is true, control continues with 1328. If 1324, control may end.

At 1328, the member is directed (e.g., via the sent invitation) to a website, such as a website hosted by the vendor of the digital pharmacy product for enrollment. The website may include a logo or other branding of the virtual pharmacy or an affiliate of the virtual pharmacy.

At 1332, the vendor may transmit a call to an API of the virtual pharmacy or targeting files to verify enrolment of the member for use of the digital pharmacy product. If verified, control continues with 1336. At 1336, the member completes the enrolment with the vendor of the digital pharmacy product. At 1340, the member downloads the digital pharmacy product (if necessary) to the user device. At 1344, the member may be mailed a user device for use of the digital pharmacy product (if necessary).

At 1348, the member sets up a profile with the vendor and begins using the digital pharmacy product (e.g., the application, the device, or a website). At 1352, the member receives the device (if sent a device) and syncs the device with one or more other devices, if necessary. At 1356, the member utilizes the digital pharmacy product. The vendor collects usage data indicative of usage of the digital pharmacy product by the member, as discussed above.

At 1364, the usage data regarding usage of the digital pharmacy product by the member (and other instances of the digital pharmacy product by other members) is shared with the virtual pharmacy, such as via a push operation from the vendor or a pull operation by the virtual pharmacy. At 1368, the virtual pharmacy may transmit a report to clients (e.g., insurance carriers) regarding utilization and trends in the usage data.

At 1360, the usage data may be analyzed (e.g., by the virtual pharmacy to determine whether a member (using the digital pharmacy product) meets one or more clinical criteria. If so, the virtual pharmacy or the TRC may reach out to the member, such as by physical mail, email, message, phone call, etc. In various implementations, the TRC may be automated and reach out automatically.

At 1372, the virtual pharmacy may bill clients for use of the digital pharmacy product by members of the client on a periodic basis, such as monthly. At 1376, the virtual pharmacy undergoes client billing reporting.

At 1380, the virtual pharmacy identifies OMS enrolment opportunities and opens instances of the OMS enrolment opportunities in a HAP (e.g., database). The HAP may be an application configured to identify and provide clinically related outreaches to members. The OMS may be computerized (e.g., for example utilizing machine learning) and include a database that includes solution related data configured to trigger designated outreaches.

Figure 14:
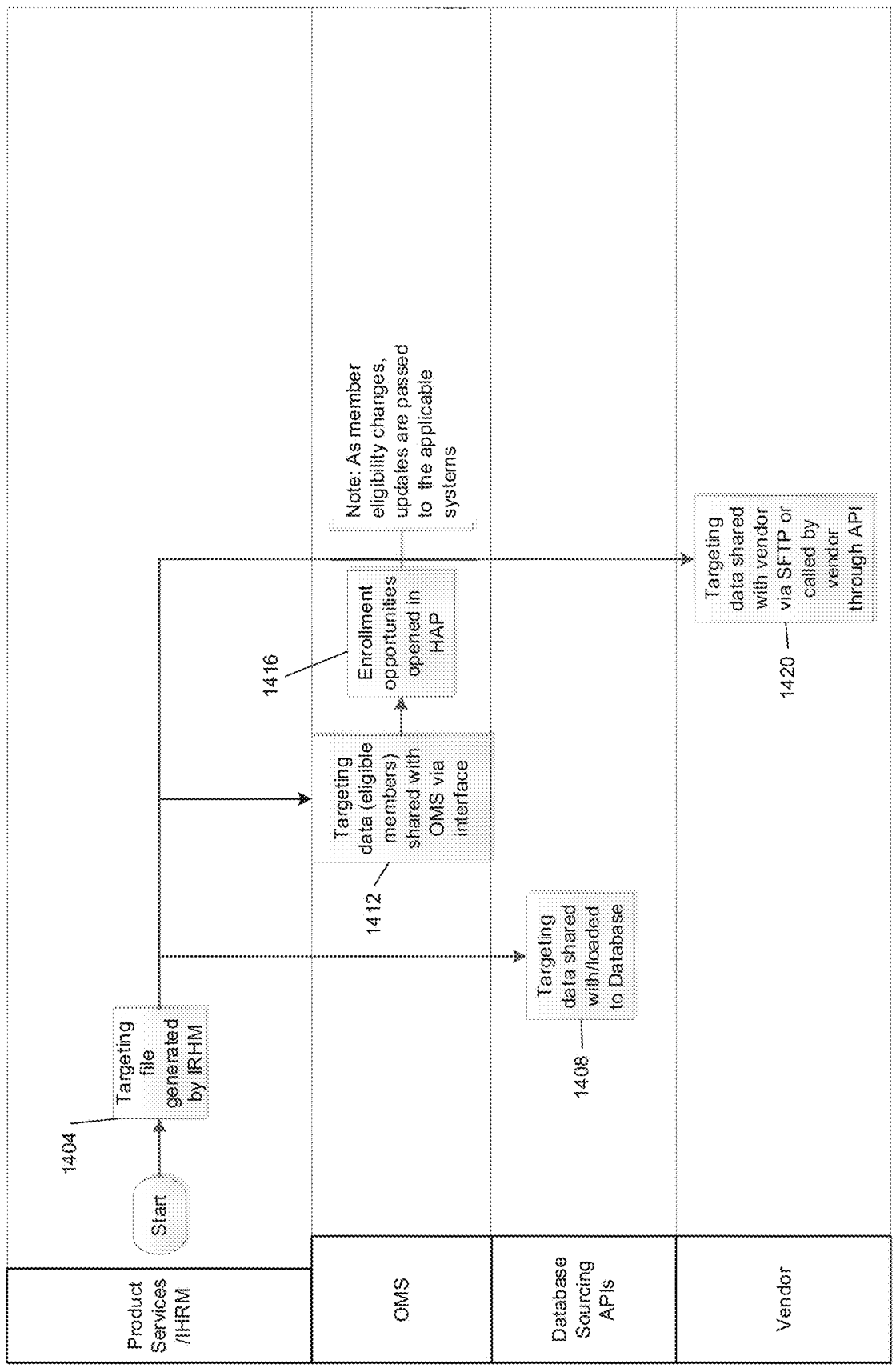
Figure 15:
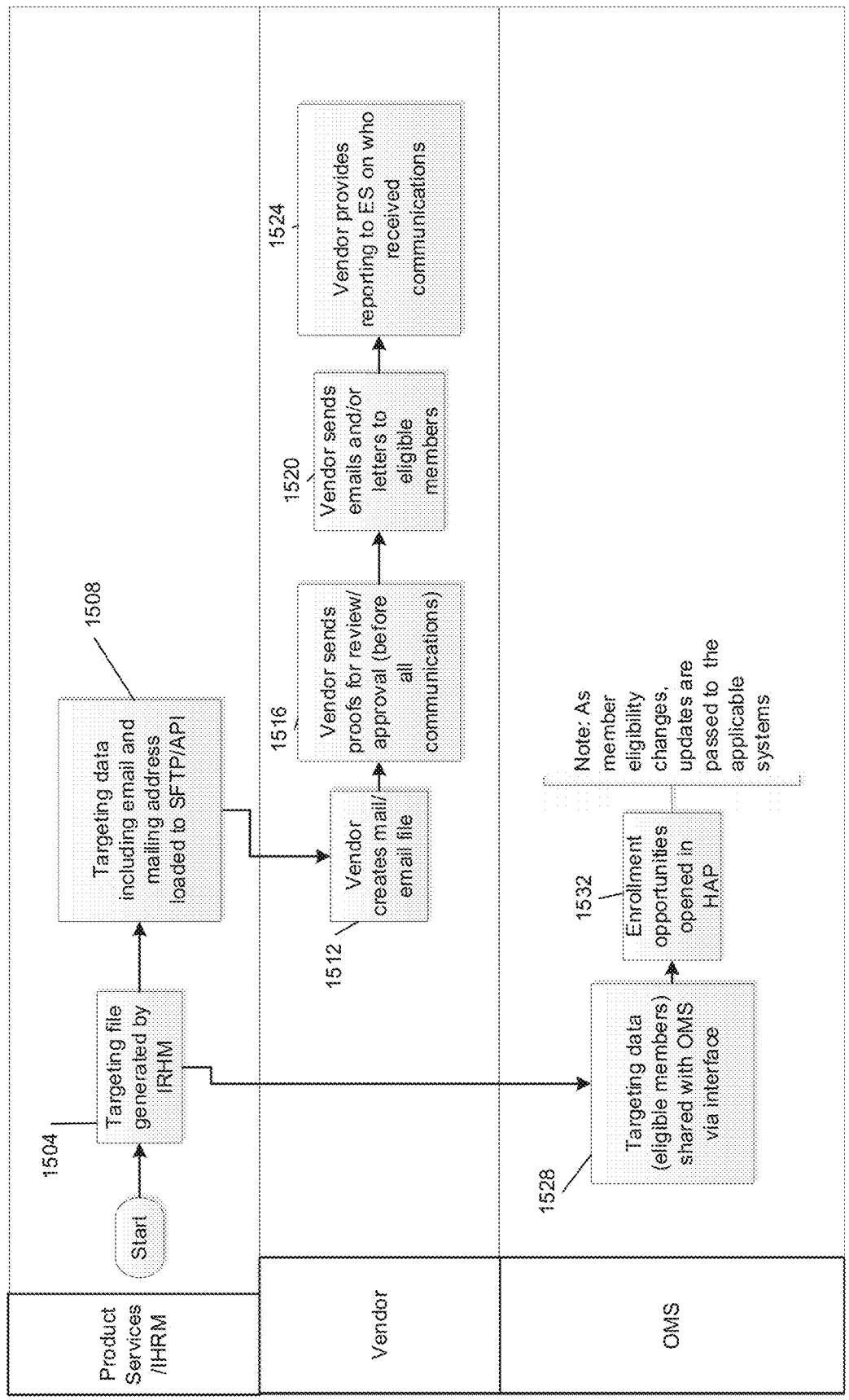

FIG. 14 is a flowchart depicting an example method of managing members for a digital pharmacy product. At 1404 a targeting file regarding targeting a member is generated by, for example, the IRHM system. At 1408, the targeting data/file is shared with or loaded to a database. At 1412, the targeting data/file (or a collection of data/files for multiple targeted members) is shared with an OSM via an interface. At 1416, entries for enrolment opportunities of the members are opened in a HAP. As member eligibility changes, updates are passed to the applicable systems, such as the OSM and the HAP. At 1420, the targeting data/file may be shared with a vendor. The sharing with the vendor may occur over a secured connection, such as through an API or using the SSH file transfer protocol (SFTP) or another suitable protocol for secure data transfer.

FIG. 14 is a flowchart depicting an example method of managing members for a digital pharmacy product. At 1504 a targeting file regarding targeting a member is generated by, for example, the IRHM system. At 1508, targeting data including an email address of the member and a physical mailing address of the member is located, for example, using the API or SFTP.

At 1512, the vendor of the digital pharmacy product creates a mail/email file for contacting the member. At 1516, the vendor sends the mail/email file to the virtual pharmacy for review and approval before contacting the member by mail or email as presented in the mail/email file. If approved, at 120 the vendor sends email and/or physical mail to the member's email address and/or mailing address. At 1524, the vendor provides the virtual pharmacy with information on who received (and/or reviewed) the communications. The vendor may track reviews of the communications sent by email.

At 1528, the targeting data/file (or a collection of data/files for multiple targeted members) is shared with an OSM via an interface. At 1532, entries for enrolment opportunities of the members are opened in a HAP. As member eligibility changes, updates are passed to the applicable systems, such as the OSM and the HAP.

Figure 16:
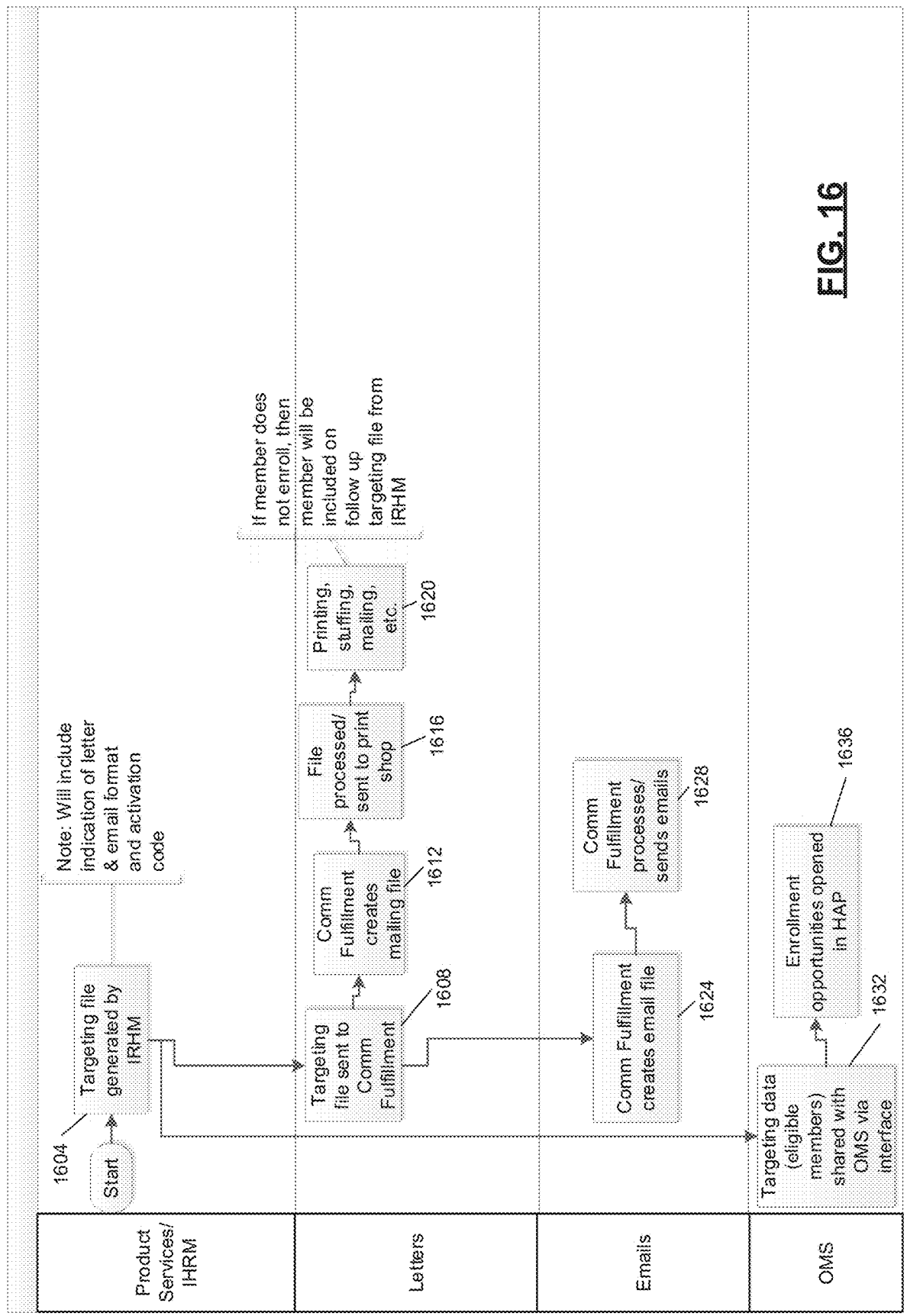

FIG. 16 is a flowchart depicting an example method of managing communication with members regarding a digital pharmacy product. At 1604 a targeting file regarding targeting a member is generated by, for example, the IRHM system. At 1608, the targeting file is transmitted to a communications (comm) system for fulfillment. The communications system may create a mailing file for mailing information regarding the digital pharmacy product to the member at 1612. At 1616, the mailing file is processed and sent to a printer (e.g., a print shop). At 1620, the mailing file is printed, stuffed into an envelope, and mailed to the member. If the member does not enroll for the digital pharmacy product, the member may be followed up with (e.g., by mail or electronically) one or more times.

At 1624, the communications system generates an email file for emailing information regarding the digital pharmacy product to the member. At 1628, the communications system sends an email including the email file to the member at the email address of the member.

At 1632, the targeting data/file (or a collection of data/files for multiple targeted members) is shared with an OSM via an interface. At 1636, entries for enrolment opportunities of the members are opened in a HAP. As member eligibility changes, updates are passed to the applicable systems, such as the OSM and the HAP.

FIG. 17 is a flowchart depicting an example method of targeting and enrolling members for use of a digital pharmacy product. At 1704, a determination is made whether a client (e.g., an insurance carrier) has opted into a program for marketing of the digital pharmacy product. If 1704 is true, control continues with 1708. At 1708, eligible members of the client are targeted by the vendor of the digital pharmacy product or the virtual pharmacy or both as discussed above via one or more communications. At 1712, a determination is made regarding whether a member is interested in enrolling. If 1712 is true, control continues with 1716.

At 1716, the member (that is interested in enrolling) is directed to (e.g., via the sent invitation) to a website, such as a website hosted by the vendor of the digital pharmacy product for enrollment. The website may include a logo or other branding of the virtual pharmacy or an affiliate of the virtual pharmacy. The vendor may interface the virtual pharmacy via an enrollment API of the virtual pharmacy or an enrolment file at 1720.

At 1724, the member completes his or her enrollment. This includes inputting valid activation criteria (e.g., an activation code), a zipcode of the member, and a date of birth (DOB) of the member. At 1728, the member agrees with terms of use (TOU) and a privacy policy (PP) for use of the digital pharmacy product. At 1732, the member downloads the digital pharmacy product (if necessary) to the user device. At 1736, the member may mail a user device for use of the digital pharmacy product (if necessary).

At 1740, the member receives the device (if sent a device) and syncs the device with one or more other devices, if necessary. At 1744, the member sets up a profile with the vendor and begins using the digital pharmacy product (e.g., the application, the device, or a website).

Conclusion

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A. The term subset does not necessarily require a proper subset. In other words, a first subset of a first set may be coextensive with (equal to) the first set.

In this application, including the definitions below, the term "module" or the term "controller" may be replaced with the term "circuit." The term "module" may refer to, be part of, or include processor hardware (shared, dedicated, or group) that executes code and memory hardware (shared, dedicated, or group) that stores code executed by the processor hardware.

The module may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are the BLUETOOTH wireless networking standard from the Bluetooth Special Interest Group and IEEE Standard 802.15.4.

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of a non-transitory computer-readable medium are nonvolatile memory devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Swift, Haskell, Go, SQL, R, Lisp, Java®, Fortran, Perl, Pascal, Curl, OCaml, JavaScript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

What is claimed is:

1. A digital health solution system, comprising:
a virtual pharmacy including one or more processors configured to operate a web portal for a user device via a network, wherein:
the web portal serves as a user interface for viewing digital health solution applications that are available for download by and activation on the user device;
the web portal is navigable to using at least one application installed on the user device; and the virtual pharmacy is configured to:
  determine whether a set of authorization criteria has been met by a user of the user device;
  in response to determining that the set of authorization criteria has been met, display a first subset of the digital health solution applications; and
  in response to determining that the set of authorization criteria has not been met:
    display a set of prompts, and
    in response to a set of user inputs corresponding to responses to the set of prompts, display a second subset of the digital health solution applications;
a digital health marketplace including one or more processors configured to:
  receive input via the network indicative of a selection of a respective application of the digital health solution applications for download and activation;
  determine whether an activation token for the respective application is cached in a cache of the digital health marketplace;
  in response to determining that the activation token for the respective application is not cached at the digital health marketplace, obtain the activation token from a developer computer of a developer of the respective application via the network; and
  transmit the activation token from the digital health marketplace to the virtual pharmacy via the network; and
a prescription fulfillment system including one or more processors configured to automatically control an automated dispensing device by:
  identifying a prescription drug associated with the respective application, and
  fulfilling the prescription drug without operator intervention by:
    controlling movement of a set of containers relative to the automated dispensing device, and
    automatically dispensing, via the automated dispensing device, the prescription drug into a container of the set of containers,
wherein the one or more processors of the virtual pharmacy are configured to transmit the activation token from the virtual pharmacy to the user device via the network, and
wherein the user device is configured to receive the activation token at the user device from the virtual pharmacy via the network and, using the activation token, at least one of download and activate the respective application.

2. The digital health solution system of claim 1 wherein the digital health marketplace is configured to select the activation token from a set of activation tokens that are cached at the digital health marketplace.

3. The digital health solution system of claim 1 wherein an activation code is used for activating the respective application after downloading.

4. The digital health solution system of claim 1 wherein the activation token includes a link to a digital distribution platform for downloading the respective application.

5. The digital health solution system of claim 4 wherein the link includes a uniform resource locator (URL).

6. The digital health solution system of claim 1, wherein:
the one or more processors of the digital health marketplace are configured to determine scores for the digital health solution applications, respectively; and
the one or more processors of the virtual pharmacy are configured to output the scores for the digital health solution applications, respectively, via the web portal.

7. The digital health solution system of claim 6 wherein the one or more processors of the digital health marketplace are configured to determine the scores for the digital health solution applications, respectively, based on at least one of usability of the digital health solution applications, technical scalability of the digital health solution applications, security of the digital health solution applications, adoption of the digital health solution applications, and empirical result data for the digital health solution applications.

8. The digital health solution system of claim 6 wherein the one or more processors of the virtual pharmacy are configured to output a tiered ranking of the digital health solution applications based on at least one of:
  the scores of the digital health solution applications, respectively; and
  clinical criteria and health benefit plan coverage.

9. The digital health solution system of claim 6 wherein the one or more processors of the digital health marketplace are configured to selectively add one of the digital health solution applications to the web portal.

10. The digital health solution system of claim 9 wherein the one or more processors of the digital health marketplace are configured to determine whether to add one of the digital health solution applications to the web portal based on at least one of clinical components of the digital health solution applications, usability components of the digital health solution applications, and values of the digital health solution applications, respectively.

11. The digital health solution system of claim 10 wherein the one or more processors of the digital health marketplace are configured to determine the values of the digital health solution applications based on returns on investment of the digital health solution applications, respectively.

12. The digital health solution system of claim 11 wherein the one or more processors of the digital health marketplace are configured to determine the returns on investment of the digital health solution applications based on efficacy models of the digital health solution applications and pricing models of the digital health solution applications, respectively.

13. The digital health solution system of claim 12 wherein the pricing models include at least one of per-person per-month costs and volume discounts.

14. The digital health solution system of claim 1 further comprising:
a benefit manager including one or more processors configured to determine a portion of a first cost of the respective application covered by a health benefit plan of a user of the user device based on an identity of the user,
wherein the one or more processors of the digital health marketplace are configured to output a final cost of the respective application to the user device based on the portion of the first cost.

15. The digital health solution system of claim 14 wherein the one or more processors of the benefit manager are configured to determine recommendations of ones of the digital health solution applications that are relevant to a user and to transmit the recommendations to a physician computer of a physician of the user.

16. The digital health solution system of claim 14 wherein the benefit manager is configured to determine recommendations using an interface developed based on Fast Healthcare Interoperability Resources (FHIR).

17. The digital health solution system of claim 1 wherein the activation token is included in an electronic prescription received from an electronic health record (EHR) system for the respective application.

18. The digital health solution system of claim 17 wherein the one or more processors of the virtual pharmacy are configured to transmit a notification to the user device in response to receipt of the electronic prescription for the respective application.

19. The digital health solution system of claim 18 wherein the notification includes at least one of a text message, a short message service (SMS) message, an email, a smartphone notification, an automated voice call, and a personal voice call.

20. The digital health solution system of claim 1 wherein the activation token is included on a prescription printed on paper.

21. The digital health solution system of claim 20 wherein the prescription printed on paper includes at least one of a uniform resource locator (URL) and a quick response (QR) code.

22. The digital health solution system of claim 1 wherein the digital health solution applications include non-generic branded digital health solution applications and generic branded digital health solution applications.

23. The digital health solution system of claim 1 wherein the one or more processors of the virtual pharmacy are configured to receive reviews of the digital health solution applications from user devices and to provide review information to the virtual pharmacy based on the reviews.

24. The digital health solution system of claim 1 wherein the one or more processors of the virtual pharmacy are configured to output usage data of the digital health solution applications to the user device via the web portal.

25. The digital health solution system of claim 24 wherein the usage data includes at least one of an average number of monthly users, a total number of lifetime users, and monthly retention percentages.

26. The digital health solution system of claim 1 wherein the one or more processors of the virtual pharmacy are configured to, in response to the determination that the set of authorization criteria has not been met:
  determine a recommendation for one or more of the digital health solution applications based on the responses to the set of prompts; and
  wherein the second subset of the digital health solution applications is based on the recommendation,
  wherein the set of authorization criteria includes a criterion that is met when no prescriptions for a user of the user device have been received.

27. The digital health solution system of claim 26 wherein the one or more processors of the virtual pharmacy are configured to determine the set of prompts using at least one of a decision tree and a decision table.

28. The digital health solution system of claim 26 wherein the virtual pharmacy includes a recommendation engine configured to receive the responses to the set of prompts as inputs and generate the recommendation as an output.

29. The digital health solution system of claim 26 wherein the recommendation includes indicators of whether the one or more of the digital health solution applications are covered for the user under a health benefit plan of the user.

30. The digital health solution system of claim 26 wherein the one or more processors of the virtual pharmacy are configured to rank the one or more of the digital health solution applications in the recommendation based on at least one of health benefit plan coverage, pricing, and information from the digital health marketplace.

31. The digital health solution system of claim 30 wherein the information from the digital health marketplace includes at least one of user feedback, social media impressions, and adoption rate.

32. The digital health solution system of claim 1 wherein the virtual pharmacy is configured to, in response to user input, filter the digital health solution applications by at least one of category, symptoms, disease state, health benefit plan coverage, and price.

33. The digital health solution system of claim 1 further comprising the user device, wherein the user device is configured to download the respective application from a digital distribution platform.

34. The digital health solution system of claim 1 further comprising the user device, wherein the user device is configured to download the respective application from a developer computer of the developer of the respective application.

35. The digital health solution system of claim 1 further comprising a developer computer of the developer of the respective application, wherein the developer computer includes one or more processors configured to:
  collect usage data for the respective application from the user device after downloading; and
  selectively transmit the collected usage data to at least one of the virtual pharmacy and the digital health marketplace.

36. The digital health solution system of claim 35 wherein the usage data includes at least one of a frequency of use of the respective application and a length of use of the respective application.

37. The digital health solution system of claim 1 wherein the one or more processors of the digital health marketplace are further configured to selectively recall one of the digital health solution applications from the virtual pharmacy, thereby rendering the recalled one of the digital health solution applications unavailable for at least one of downloading and activation via the virtual pharmacy.

38. A digital health solution system, comprising:
  a virtual pharmacy including one or more processors configured to operate a web portal for a user device via a network, wherein:
    the web portal serves as a user interface for viewing digital health solution applications that are available for download by and activation on the user device;
    the web portal is navigable to using at least one application installed on the user device; and
    the virtual pharmacy is configured to:
      determine whether a set of authorization criteria has been met by a user of the user device;
      in response to determining that the set of authorization criteria has been met, display a first subset of the digital health solution applications; and
      in response to determining that the set of authorization criteria has not been met:
        display a set of prompts, and
        in response to a set of user inputs corresponding to responses to the set of prompts, display a second subset of the digital health solution applications;
  a digital health marketplace including one or more processors configured to:
    receive input via the network indicative of a selection of a respective application of the digital health solution applications, determine whether an activation token for a respective application of the digital health solution applications is cached in a cache at the digital health marketplace;
in response to determining that the activation token for the respective application is not cached at the digital health marketplace, obtain the activation token from the user device at the virtual pharmacy via the network, and
transmit the activation token from the virtual pharmacy to the digital health marketplace via the network; and
a prescription fulfillment system including one or more processors configured to automatically control an automated dispensing device by:
identifying a prescription drug associated with the respective application, and
fulfilling the prescription drug without operator intervention by:
controlling movement of a set of containers relative to the automated dispensing device, and
automatically dispensing, via the automated dispensing device, the prescription drug into a container of the set of containers,
wherein the one or more processors of the digital health marketplace are configured to transmit the activation token from the digital health marketplace to a developer computer of a developer of the respective application via the network,
wherein the developer computer is configured to allow the user device to download the respective application in response to receipt of the activation token from the digital health marketplace.

39. A method of distributing digital health solution applications, the method comprising:
by a virtual pharmacy implemented on one or more processors, operating a web portal for a user device via a network, wherein:
the web portal serves as a user interface for viewing digital health solution applications that are available for download by and activation on the user device;
the web portal is navigable to using at least one application on the user device; and
the virtual pharmacy is configured to:
determine whether a set of authorization criteria has been met by a user of the user device;
in response to determining that the set of authorization criteria has been met, display a first subset of the digital health solution applications; and
in response to determining that the set of authorization criteria has not been met:
display a set of prompts, and
in response to a set of user inputs corresponding to responses to the set of prompts, display a second subset of the digital health solution applications;
by a digital health marketplace:
receiving input via the network indicative of a selection of a respective application of the digital health solution applications for download and activation;
determining whether an activation token for the respective application is cached in a cache at the digital health marketplace;
in response to determining that the activation token for the respective application is not cached at the digital health marketplace, obtaining the activation token for the respective application from a developer of the respective application via the network; and
transmitting the activation from the digital health marketplace to the virtual pharmacy via the network;
by the virtual pharmacy, transmitting the activation token from the virtual pharmacy to the user device via the network;
by the user device, receiving the activation token at the user device from the virtual pharmacy via the network and, using the activation token, at least one of downloading and activating the respective application; and
by a prescription fulfillment system including one or more processors, automatically controlling an automated dispensing device by:
identifying a prescription drug associated with the respective application, and
fulfilling the prescription drug without operator intervention by:
controlling movement of a set of containers relative to the automated dispensing device, and
automatically dispensing, via the automated dispensing device, the prescription drug into a container of the set of containers.

40. A method of distributing digital health solution applications, the method comprising:
by a virtual pharmacy including one or more processors, operating a web portal for a user device via a network, wherein:
the web portal serves as a user interface for viewing digital health solution applications that are available for download by and activation on the user device;
the web portal is navigable to using at least one application installed on the user device; and
the virtual pharmacy is configured to:
determine whether a set of authorization criteria has been met by a user of the user device;
in response to determining that the set of authorization criteria has been met, display a first subset of the digital health solution applications; and
in response to determining that the set of authorization criteria has not been met:
display a set of prompts, and
in response to a set of user inputs corresponding to responses to the set of prompts, display a second subset of the digital health solution applications;
by a digital health marketplace including one or more processors, communicating with developer computers of developers of the digital health solution applications;
by the one or more processors of the virtual pharmacy:
receiving user input via the network indicative of a selection of respective application of the digital health solution applications,
determining whether an activation token for the respective application is cached in a cache at the digital health marketplace;
in response to determining that the activation token for the respective application is not cached at the digital health marketplace, obtaining the activation token for the respective application from the user device via the network, and
transmitting the activation token from the virtual pharmacy to the digital health marketplace via the network;
by the one or more processors of the digital health marketplace, transmitting the activation token from the digital health marketplace to a developer computer of a developer of the respective application via the network;

by the developer computer, allowing the user device to download the respective application in response to receipt of the activation token from the digital health marketplace; and by a prescription fulfillment system including one or more processors, automatically controlling an automated dispensing device by:
  identifying a prescription drug associated with the respective application, and
  fulfilling the prescription drug without operator intervention by:
    controlling movement of a set of containers relative to the automated dispensing device, and
    automatically dispensing, via the automated dispensing device, the prescription drug into a container of the set of containers.

* * * * *